(12) United States Patent
Belousov

(10) Patent No.: US 12,343,574 B2
(45) Date of Patent: Jul. 1, 2025

(54) BREATHING APPARATUS WITH MULTIPLE BREATHING CHANNELS

(71) Applicant: MPOINTAERO INC., Fairfax, VA (US)

(72) Inventor: Maksim Belousov, Leningrad (RU)

(73) Assignee: MPOINTAERO Inc., Fairfax, VA (US)

(*) Notice: Subject to any disclaimer, the term of this patent is extended or adjusted under 35 U.S.C. 154(b) by 0 days.

(21) Appl. No.: 18/300,571

(22) Filed: Apr. 14, 2023

(65) Prior Publication Data

US 2024/0342418 A1 Oct. 17, 2024

Related U.S. Application Data

(63) Continuation of application No. 17/350,602, filed on Jun. 17, 2021, now Pat. No. 11,654,310, which is a continuation of application No. PCT/US2021/022592, filed on Mar. 16, 2021.

(60) Provisional application No. 62/990,279, filed on Mar. 16, 2020, provisional application No. 63/198,865, filed on Nov. 18, 2020.

(51) Int. Cl.
| | | |
|---|---|---|
| A62B 23/02 | (2006.01) | |
| A61M 16/06 | (2006.01) | |
| A61M 16/20 | (2006.01) | |
| A62B 7/00 | (2006.01) | |
| A62B 9/02 | (2006.01) | |
| A62B 18/02 | (2006.01) | |

(52) U.S. Cl.
CPC ....... *A62B 23/025* (2013.01); *A61M 16/0666* (2013.01); *A61M 16/208* (2013.01); *A62B 7/00* (2013.01); *A62B 9/02* (2013.01); *A62B 18/025* (2013.01); *A61M 2210/0618* (2013.01)

(58) Field of Classification Search
CPC ............ A62B 23/00–025; A62B 23/06; A62B 7/00–14; A62B 9/00–06; A62B 18/00–10
See application file for complete search history.

(56) References Cited

U.S. PATENT DOCUMENTS

| | | | |
|---|---|---|---|
| 1,946,744 | A | 2/1934 | Jones et al. |
| 2,290,323 | A | 7/1942 | Graham |
| 3,216,415 | A | 11/1965 | Littleton |

(Continued)

FOREIGN PATENT DOCUMENTS

| | | | |
|---|---|---|---|
| CN | 2162260 Y | 4/1994 | |
| CN | 1531879 A | 9/2004 | |

(Continued)

OTHER PUBLICATIONS

Decision of Rejection for Japanese Application No. 2019-566174, mailed Nov. 15, 2023, 9 pages.

(Continued)

*Primary Examiner* — Justine R Yu
*Assistant Examiner* — Jacqueline M Pinderski
(74) *Attorney, Agent, or Firm* — COOLEY LLP

(57) ABSTRACT

The present disclosure relates generally to breathing apparatuses where inhaled air and exhaled air are separated into different channels to permit a user to inhale fresh air. These devices can optionally filter inhaled air and exhaled air. These devices may include valves to help guide inhaled air and exhaled air to desired locations.

28 Claims, 32 Drawing Sheets

(56) References Cited

U.S. PATENT DOCUMENTS

| | | | |
|---|---|---|---|
| 3,288,138 A | 11/1966 | Louis et al. | |
| 3,353,337 A | 11/1967 | Gale | |
| 4,196,728 A | 4/1980 | Granite | |
| 4,458,679 A | 7/1984 | Ward | |
| 4,612,025 A | 9/1986 | Sampey | |
| 4,848,366 A | 7/1989 | Aita et al. | |
| 4,856,509 A | 8/1989 | Lemelson | |
| 4,915,105 A | 4/1990 | Lee | |
| 5,018,519 A * | 5/1991 | Brown | A61M 16/0616 128/203.29 |
| 5,372,621 A | 12/1994 | Staton et al. | |
| 5,419,318 A | 5/1995 | Tayebi | |
| 5,584,286 A * | 12/1996 | Kippax | A62B 7/00 128/200.24 |
| 6,055,666 A | 5/2000 | Eklund et al. | |
| 6,102,040 A | 8/2000 | Tayebi et al. | |
| 6,478,026 B1 | 11/2002 | Wood | |
| 6,718,981 B2 | 4/2004 | Cardarelli | |
| 6,868,852 B2 | 3/2005 | Gaschke | |
| 8,166,972 B2 * | 5/2012 | Daliri | A61M 16/1055 128/204.23 |
| 8,347,886 B2 | 1/2013 | Ho et al. | |
| 8,397,724 B2 * | 3/2013 | Sher | A61M 16/06 128/205.24 |
| 10,625,102 B1 | 4/2020 | Chen | |
| 11,071,336 B2 | 7/2021 | Belousov et al. | |
| 11,654,310 B2 * | 5/2023 | Belousov | A62B 18/084 128/206.19 |
| 2004/0003810 A1 | 1/2004 | Templeton et al. | |
| 2004/0226563 A1 * | 11/2004 | Xu | A62B 18/02 128/206.23 |
| 2006/0237017 A1 * | 10/2006 | Davidson | A61M 16/06 128/205.25 |
| 2007/0125237 A1 | 6/2007 | Park | |
| 2008/0245364 A1 | 10/2008 | Patterson | |
| 2009/0211583 A1 | 8/2009 | Carroll et al. | |
| 2010/0071699 A1 | 3/2010 | Campbell et al. | |
| 2013/0019879 A1 | 1/2013 | Hsu | |
| 2013/0152930 A1 | 6/2013 | Votel et al. | |
| 2014/0245524 A1 | 9/2014 | Stephens | |
| 2014/0373846 A1 | 12/2014 | Kao et al. | |
| 2015/0139894 A1 | 5/2015 | Fontanez et al. | |
| 2015/0217146 A1 | 8/2015 | Skov et al. | |
| 2016/0023127 A1 | 1/2016 | Park et al. | |
| 2016/0058081 A1 | 3/2016 | Lee | |
| 2017/0035979 A1 | 2/2017 | Pedro et al. | |
| 2017/0157435 A1 | 6/2017 | Choi | |
| 2017/0189878 A1 | 7/2017 | Fontanez et al. | |
| 2018/0007982 A1 | 1/2018 | Reese et al. | |
| 2018/0296864 A1 | 10/2018 | Feasey et al. | |
| 2019/0009114 A1 | 1/2019 | Han | |
| 2019/0060811 A1 | 2/2019 | Reuben | |
| 2020/0121005 A1 | 4/2020 | Belousov et al. | |
| 2020/0406069 A1 * | 12/2020 | Fu | A62B 23/02 |
| 2021/0346737 A1 | 11/2021 | Belousov | |
| 2022/0032095 A1 | 2/2022 | Belousov et al. | |

FOREIGN PATENT DOCUMENTS

| | | | |
|---|---|---|---|
| CN | 201551699 U | 8/2010 | |
| CN | 103736221 A | 4/2014 | |
| CN | 104093457 A | 10/2014 | |
| CN | 104258514 A | 1/2015 | |
| CN | 204132474 U | 2/2015 | |
| CN | 106473272 A | 3/2017 | |
| CN | 106723522 A | 5/2017 | |
| CN | 107048537 A | 8/2017 | |
| CN | 111163842 A | 5/2020 | |
| EP | 1322384 B1 | 12/2007 | |
| EP | 3159045 A1 | 4/2017 | |
| GB | 261470 * | 11/1926 | A62B 18/00 |
| GB | 261470 A | 11/1926 | |
| JP | 2005185381 A | 7/2005 | |
| JP | 2008113922 A | 5/2008 | |
| KR | 200177011 Y1 | 4/2000 | |
| KR | 20050042986 A | 5/2005 | |
| KR | 20160089185 A | 7/2016 | |
| KR | 20180001822 A | 1/2018 | |
| KR | 20190119458 A | 10/2019 | |
| RU | 2062139 C1 | 6/1996 | |
| RU | 2187232 C2 | 8/2002 | |
| RU | 32368 U1 | 9/2003 | |
| RU | 2240160 C1 | 11/2004 | |
| RU | 2641133 C1 | 1/2018 | |
| RU | 2651260 C2 | 4/2018 | |
| SU | 28276 A1 | 11/1932 | |
| SU | 413965 A1 | 2/1974 | |
| SU | 844026 A2 | 7/1981 | |
| SU | 980780 A1 | 12/1982 | |
| SU | 1784234 A1 | 12/1992 | |
| WO | WO-2007012060 A2 | 1/2007 | |
| WO | WO-2008109438 A2 | 9/2008 | |
| WO | WO-2012044113 A2 | 4/2012 | |
| WO | WO-2014185700 A1 | 11/2014 | |
| WO | WO-2015131876 A1 | 9/2015 | |
| WO | WO-2018199694 A1 | 11/2018 | |
| WO | WO-2018222081 A1 | 12/2018 | |
| WO | WO-2019039963 A1 | 2/2019 | |
| WO | WO-2019071296 A1 | 4/2019 | |
| WO | WO-2020076195 A1 | 4/2020 | |
| WO | WO-2021113379 A1 | 6/2021 | |
| WO | WO-2021188560 A1 | 9/2021 | |

OTHER PUBLICATIONS

Notice of Preliminary Rejection for Korean Application No. 10-2019-7038505, dated Jun. 30, 2023, 13 pages.
Office Action for Brazilian Application No. 20191125140 dated Oct. 23, 2023, 4 pages.
Second Office Action and Search report for Chinese Application No. 201880054230.2 dated Oct. 17, 2023, 17 pages.
Extended European Search Report for European Application No. 18810853.4, mailed Feb. 11, 2021, 7 pages.
International Preliminary Report on Patentability for International Application No. PCT/RU2018/000267, dated Dec. 3, 2019, 4 pages.
International Preliminary Report on Patentability for International Application No. PCT/RU2018/000268, dated Apr. 25, 2019, 12 pages.
International Search Report and Written Opinion for International Application No. PCT/RU2018/000267, mailed Sep. 20, 2018, 11 pages.
International Search Report and Written Opinion for International Application No. PCT/RU2018/000268, mailed Sep. 6, 2018, 7 pages.
International Search Report and Written Opinion for International Application No. PCT/RU2019/050177, mailed Jan. 30, 2020, 12 pages.
International Search Report and Written Opinion for International Application No. PCT/US2020/062916, mailed Mar. 22, 2021, 11 pages.
International Search Report and Written Opinion for International Application No. PCT/US2021/022592, mailed Jul. 21, 2021, 16 pages.
Notice of Reasons for Rejection for Japanese Application No. 20190566174, mailed Jun. 16, 2022, 8 pages.
Office Action and Search Report for Chinese Application No. 20218035691 dated Apr. 25, 2023, 23 pages.
Office Action for Brazilian Application No. 112019025140-5, dated Sep. 13, 2022, 5 pages.
Office Action for Chinese Application No. 20188054230 dated Dec. 23, 2022, 6 pages.
Office Action for European Application No. 18810853.4, mailed Nov. 4, 2022, 4 pages.
Office Action for Japanese Application No. 2019-566174 mailed Mar. 31, 2023, 8 pages.
Office Action for Mexican Application No. MX/a/2019/014185 dated Apr. 27, 2023, 6 pages.

(56) References Cited

OTHER PUBLICATIONS

Office Action for U.S. Appl. No. 16/700,756, mailed Aug. 6, 2020, 14 pages.
Office Action for U.S. Appl. No. 17/350,602, mailed Mar. 24, 2022, 36 pages.
Office Action for U.S. Appl. No. 17/350,602, mailed Nov. 8, 2021, 29 pages.
Office Action for U.S. Appl. No. 17/350,602, mailed Nov. 9, 2022, 32 pages.
Second Office Action and Search report for Chinese Application No. 202180035691.7 dated Jan. 26, 2024, 21 pages.
Rejection Decision for Chinese Application No. 202180035691.7, mailed Nov. 27, 2024, with English translation, 16 pages.
Office Action for U.S. Appl. No. 17/283,468 mailed Jul. 5, 2024, 5 pages.
Office Action for Brazilian Application No. 20191125140 mailed May 28, 2024, 6 pages.
Office Action for Canadian Application No. 3100189, dated Sep. 10, 2024, 3 pages.
Office Action for Chinese Application No. 202180035691.7 mailed Jul. 3, 2024, 14 pages.

\* cited by examiner

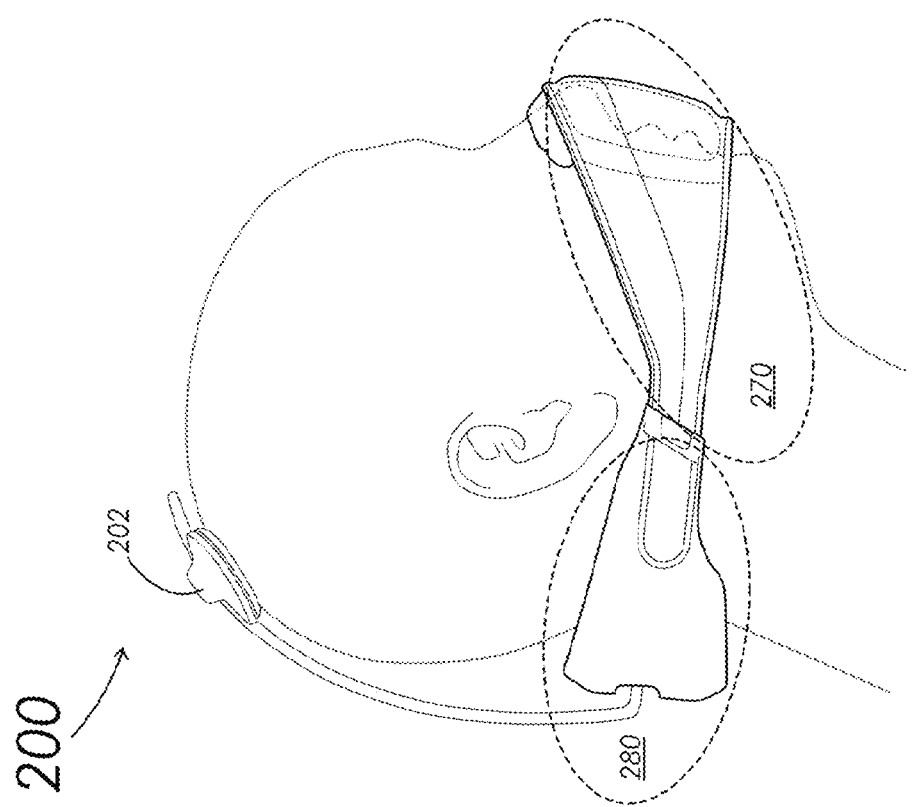
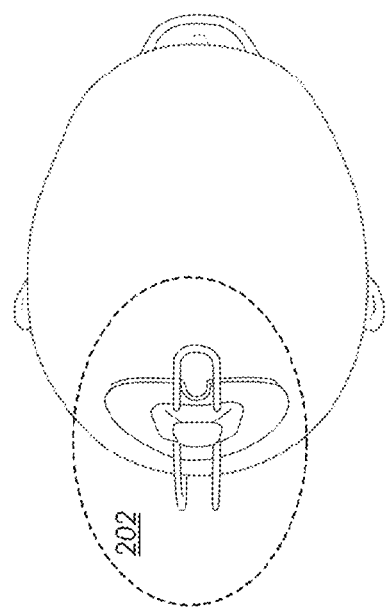
FIG. 2A
FIG. 2B

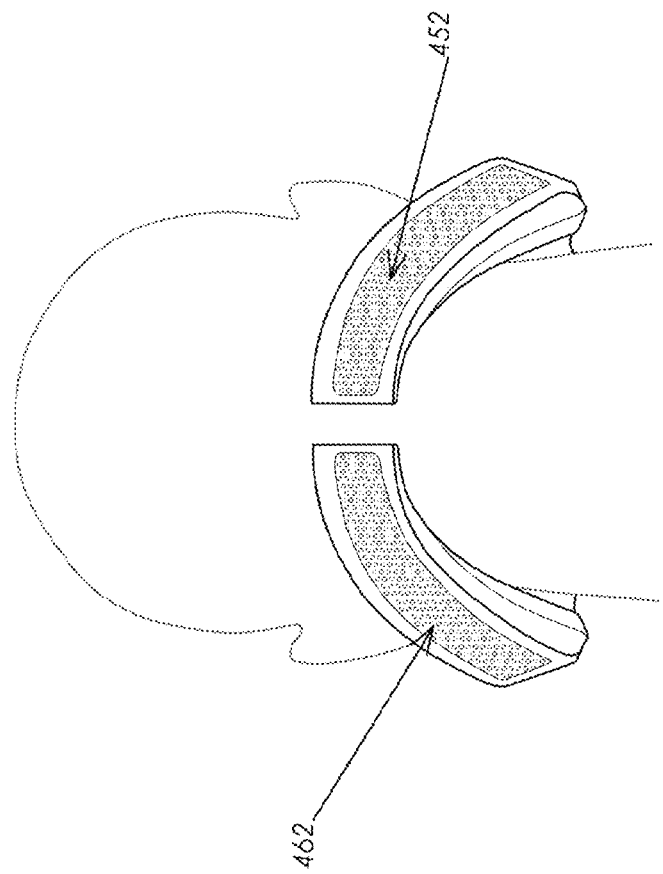
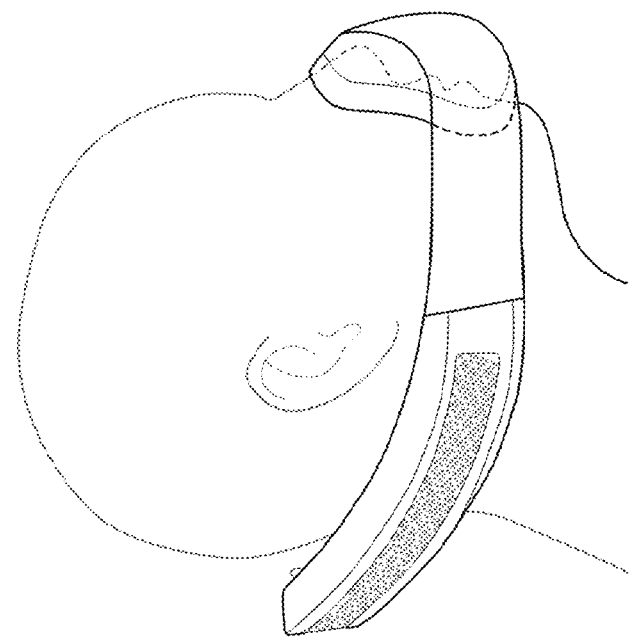
FIG. 4D
FIG. 4C

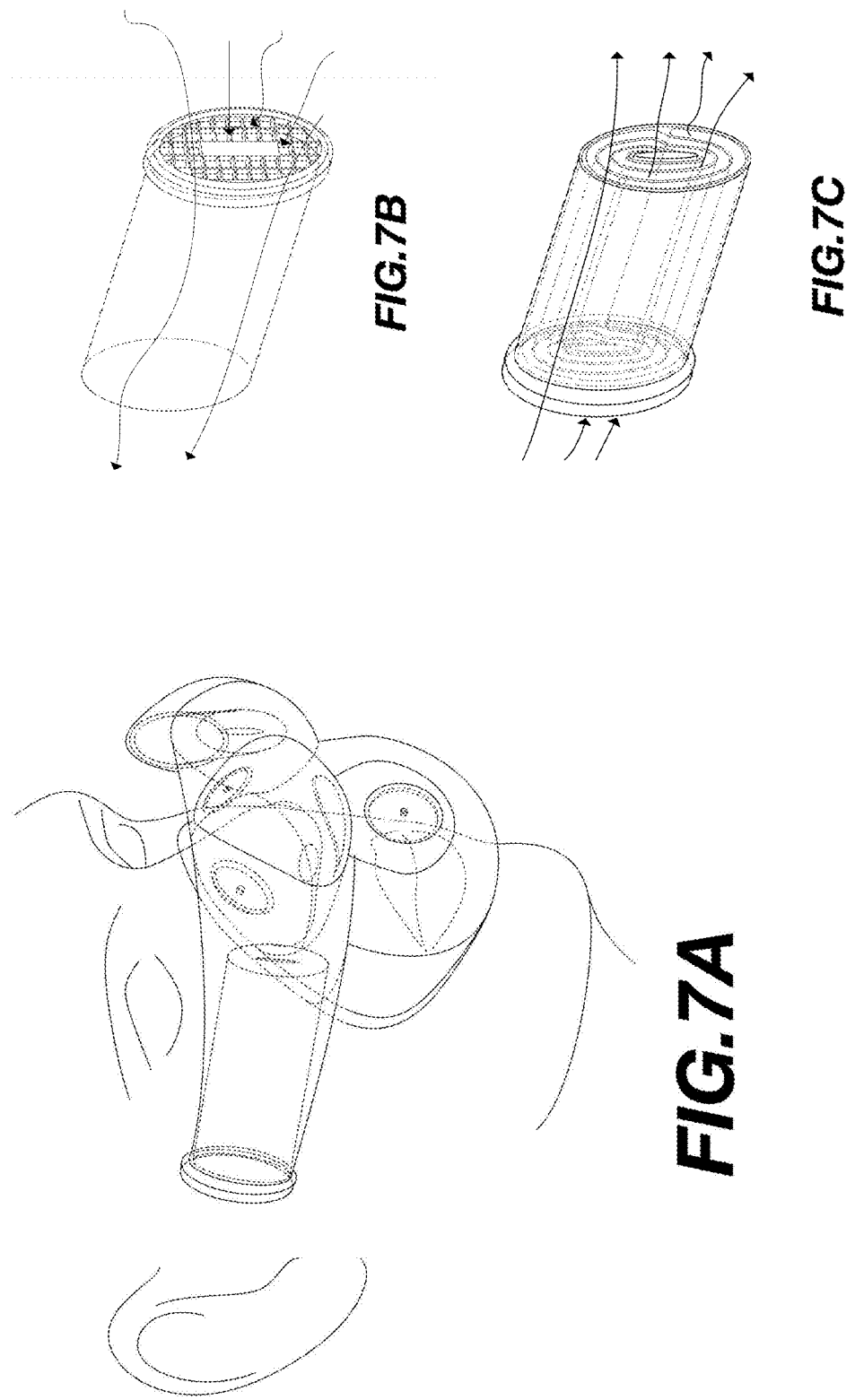

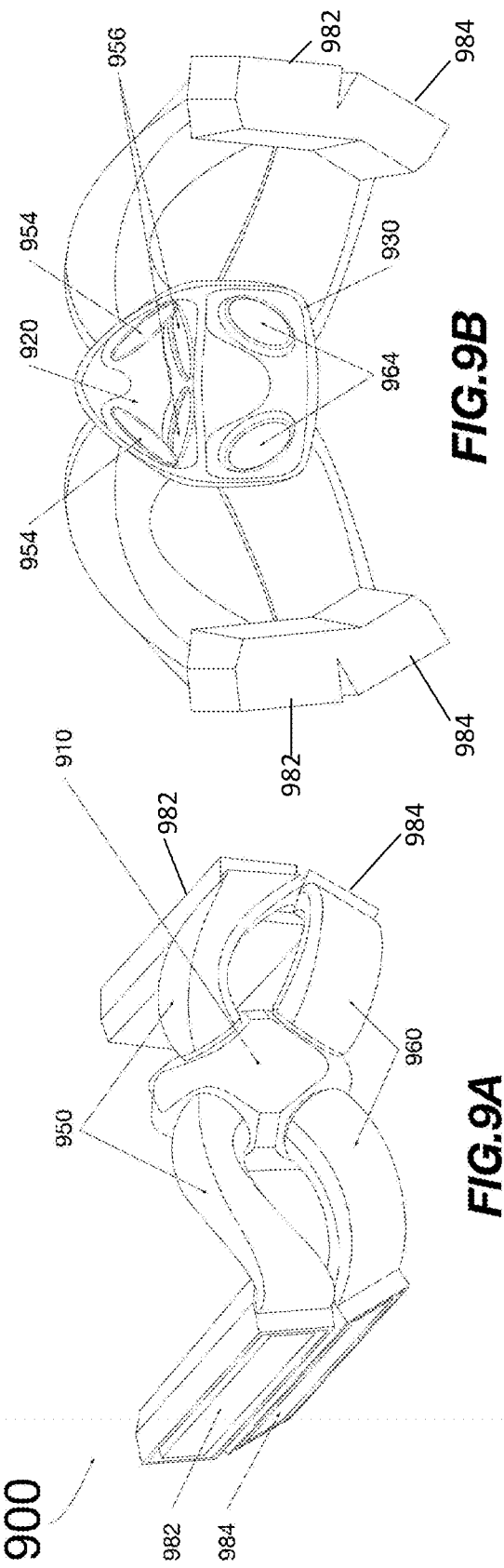

BREATHING APPARATUS WITH MULTIPLE BREATHING CHANNELS

This application is a continuation U.S. patent application Ser. No. 17/350,602, filed Jun. 17, 2023, now U.S. Pat. No. 11,654,310, which is a continuation application of International Patent Application No. PCT/US2021/022592, filed on Mar. 16, 2021, which claims priority to and the benefit of U.S. Provisional Patent Application No. 62/990,279, filed on Mar. 16, 2020, and U.S. Provisional Patent Application No. 63/198,865, filed on Nov. 18, 2020, the disclosure of each of which is hereby incorporated by reference in its entirety.

FIELD OF THE INVENTION

The present disclosure relates generally to breathing apparatuses with separate channels for inhaled air and exhaled air.

BACKGROUND

Today, three types of respirators are used as Respiratory Protective Devices (RPD) for respiratory organs: (1) a first type has an exhalation valve, and replaceable filtering elements (cartridges) that are installed in a housing made of plastic and silicone (reusable); (2) a second type has an exhalation valve and a filter housing made of filter material; and (3) a third type has a filter housing made of filter material without an exhalation valve, and inhalation and exhalation are filtered by the respirator housing.

There are a few disadvantages associated with these respirators. One disadvantage is that the under-mask space is closed, which forms the volumetric dead zone during breathing. This leads to an increased content of carbon dioxide in the inhaled air, increase in air humidity and temperature. As a result, increased fatigue, sweating, irritation of the facial skin. Another disadvantage is that a shared breathing air volume is created for the nose and mouth, which makes the use of respirators uncomfortable even in a state of calm. The coronavirus pandemic has exacerbated the disadvantages of these respirators. Accordingly, there is a need for a new type of respirators.

SUMMARY

In one aspect, the present disclosure provides a respirator, comprising: (i) a mouth aperture configured to be disposed about a mouth of a user; (ii) a nasal aperture configured to be disposed about a pair of nostrils of the user when the mouth aperture is disposed about the mouth of the user; (iii) a nasal fluid channel extending between the nasal aperture and a nasal inlet; (iv) an oral fluid channel extending from the mouth aperture to an oral outlet, such that fluidic communication between the nasal fluid channel and the oral fluid channel is prevented; (v) a nasal inhalation valve disposed within the nasal fluid channel between the nasal aperture and the nasal inlet and configured to transition between (a) an open configuration in which the nasal aperture is in fluidic communication with the nasal inlet to allow the user to inhale from the nasal inlet to the pair of nostrils, and (b) a closed configuration in which fluidic communication between the nasal aperture and the nasal inlet is prevented, the nasal inhalation valve configured to assume its open configuration in response to nasal inhalation by the user, and its closed configuration in response to nasal exhalation by the user; (vi) a nasal exhalation valve configured to transition between (a) an open configuration in which the nasal fluid channel is in fluidic communication with the oral fluid channel or an environment to allow the user to exhale from the pair of nostrils to the oral fluid channel or the environment, and (b) a closed configuration in which air is prevented from passing through the nasal exhalation valve, the nasal exhalation valve configured to assume its open configuration in response to nasal exhalation by the user, and its closed configuration in response to nasal inhalation by the user; and (vii) an oral exhalation valve disposed within the oral fluid channel between the mouth aperture and the oral outlet and configured to transition between (a) an open configuration in which the mouth aperture is in fluidic communication with the oral outlet, and (b) a closed configuration in which fluidic communication between the mouth aperture and the oral outlet is prevented.

In another aspect, the present disclosure provides (i) a mouth aperture configured to be disposed about a mouth of a user; (ii) a nasal aperture configured to be disposed about a pair of nostrils of the user when the mouth aperture is disposed about the mouth of the user; (iii) a nasal fluid reservoir configured to be in fluidic communication with the pair of nostrils; (iv) an oral fluid reservoir configured to be in fluidic communication with the mouth of the user; (v) a nasal inhalation valve disposed between the nasal fluid reservoir and an inhalation channel that is in fluidic communication with an inhalation inlet, and configured to transition between (a) an open configuration in which the nasal fluid reservoir is in fluidic communication with the inhalation channel, and (b) a closed configuration in which fluidic communication between the nasal fluid reservoir and the inhalation channel is prevented; (vi) a nasal exhalation valve disposed between the nasal fluid reservoir and an exhalation channel that is in fluidic communication with an exhalation outlet, and configured to transition between (a) an open configuration in which the nasal fluid reservoir is in fluidic communication with the exhalation channel, and (b) a closed configuration in which fluidic communication between the nasal fluid reservoir and the exhalation channel is prevented; (vii) an oral inhalation valve disposed between the oral fluid reservoir and the inhalation channel, and configured to transition between (a) an open configuration in which the oral fluid reservoir is in fluidic communication with the inhalation channel, and (b) a closed configuration in which fluidic communication between the oral fluid reservoir and the inhalation channel is prevented; and (viii) an oral exhalation valve disposed between the oral fluid reservoir and the exhalation channel, and configured to transition between (a) an open configuration in which the oral fluid reservoir is in fluidic communication with the exhalation channel, and (b) a closed configuration in which fluidic communication between the oral fluid reservoir and the exhalation channel is prevented. The nasal inhalation valve is configured to assume (a) its open configuration in response to nasal inhalation by the user, and (b) its closed configuration in response to nasal exhalation by the user. The nasal exhalation valve is configured to assume (a) its open configuration in response to nasal exhalation by the user, and (b) its closed configuration in response to nasal inhalation by the user. The oral inhalation valve is configured to assume (a) its open configuration in response to oral inhalation by the user, and (b) its closed configuration in response to oral inhalation by the user. The oral exhalation valve is configured to assume (a) its open configuration in response to oral exhalation by the user, and (b) its closed configuration in response to oral inhalation by the user.

In yet another aspect, the present disclosure provides a respirator comprising: (i) a mouth aperture configured to be disposed about a mouth of a user; (ii) a nasal aperture configured to be disposed about a pair of nostrils of the user when the mouth aperture is disposed about the mouth of the user; (iii) a nasal fluid channel extending between the nasal aperture and a nasal inlet; and (iv) an inhalation filter disposed between the nasal inlet and the nostrils, the inhalation filter being configured to include a liquid medium.

BRIEF DESCRIPTION OF THE FIGURES

FIG. 2A is a side view of a respirator 200, in accordance with an embodiment of FIG. 1.

FIG. 2B is a top-down view of the respirator 200 of FIG. 2A.

FIG. 4C is a side view of the respirator 400.

FIG. 4D is a rear view of the respirator 400.

FIG. 5A shows a front view, FIG. 5B a side view, and FIG. 5C a rear view. The respirator 500 can be secured to a user's head and face using any known mechanism, including but not limited to straps, mounts, and ear loops. The respirator 500 can be secured to a user's head and face using the head mounts described in FIG. 2A or FIG. 4D.

FIG. 6A shows a front view, FIG. 6B a side view, and FIG. 6C a rear view.

FIG. 7A is an illustration of a respirator having roll filters as inhalation filters.

FIGS. 7B and 7C are an illustration of a roll filter. The arrows show the directions of air flow.

FIG. 9A is a front view of a respirator 900, in accordance with an embodiment of FIG. 1.

FIG. 9B is a rear view of the respirator 900.

FIG. 15B shows an obturator 1528 of the hydro-respirator 1500.

DETAILED DESCRIPTION

The present disclosure describes embodiments of respirators with separate channels for inhaled air and exhaled air, thereby providing a user with better breathing experience than existing respirators. As used herein, the term "channel" means three-dimensional space enclosed by a closed surface. A channel can have a regular or irregular shape. The term "channel" does not mean that it must be elongated. In some implementations, a channel is elongated. In some implementations, a channel is not elongated. For example, a channel can be a chamber in some implementations.

Figure 1:
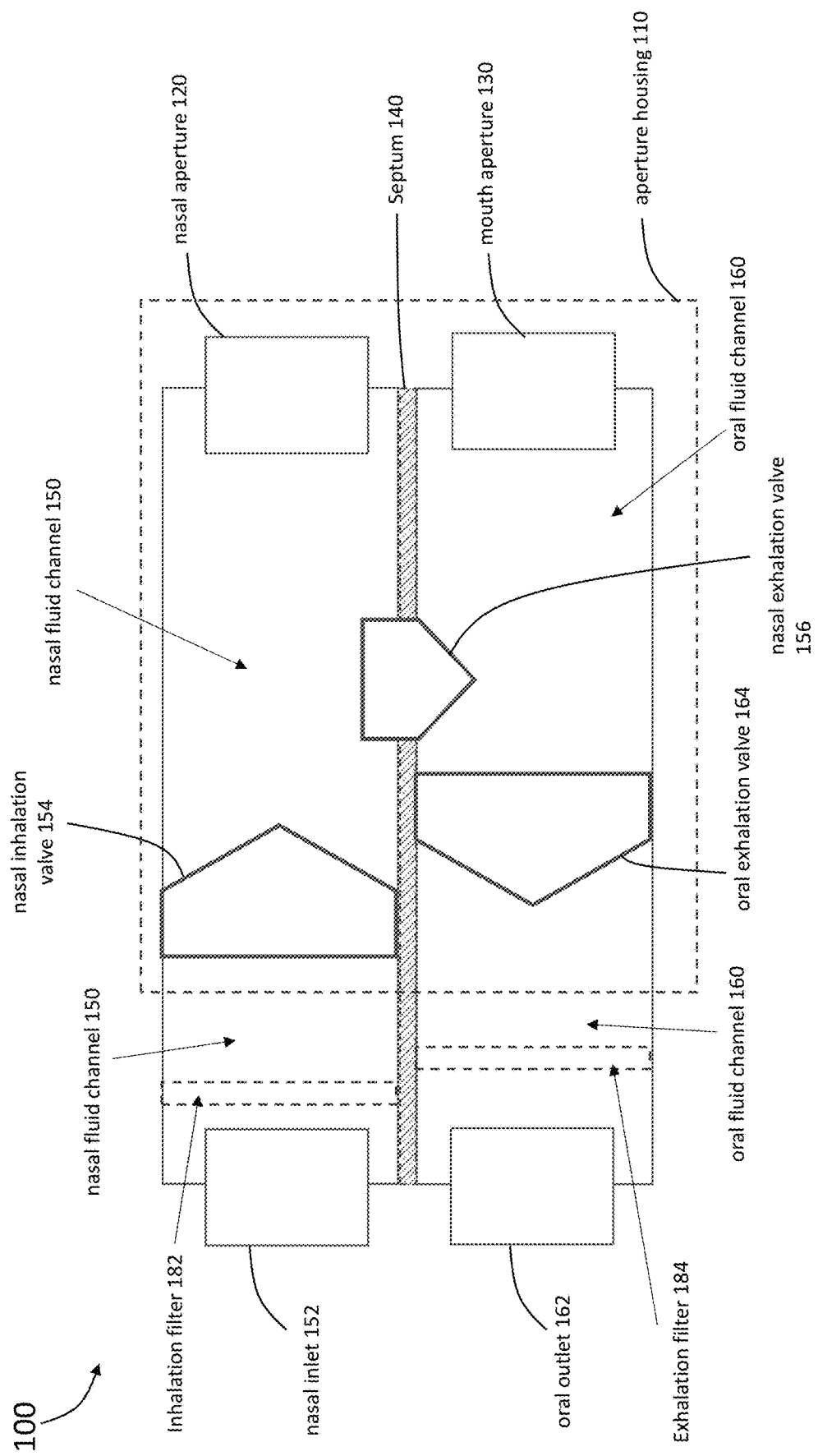
FIG. 1 is a schematic diagram illustrating a respirator 100, in accordance with an embodiment.

As shown in FIG. 1, the respirator 100 comprises: (a) a nasal aperture 120, (b) a mouth aperture 130, (c) a nasal fluid channel 150, (d) a nasal inlet 152, (e) a nasal inhalation valve 154, (f) a nasal exhalation valve 156, (g) an oral fluid channel 160, (h) an oral outlet 162, and (i) an oral exhalation valve 164.

The nasal aperture 120 is configured to be disposed about a pair of nostrils of a user. The mouth aperture 130 is configured to be disposed about a mouth of the user when the nasal aperture 120 is disposed about the nostrils of the user. The respirator 100 can further comprise an obturator (not shown) disposed on the circumferences of the nasal aperture 120 and the mouth aperture 130. The obturator is configured to form a seal around the nostrils and the mouth so that fluidic communication between the nasal fluid channel 150 and the oral fluid channel 160 is prevented unless the nasal exhalation valve 156 is in an open configuration.

The nasal fluid channel 150 extends between the nasal aperture 120 and the nasal inlet 152. The oral fluid channel 160 extends between the mouth aperture 130 and the oral outlet 162. The nasal inhalation valve 154 is disposed within the nasal fluid channel 150 between the nasal aperture 120 and the nasal inlet 152. The nasal inhalation valve 154 is configured to transition between an open configuration and a closed configuration. In the open configuration, the nasal aperture 120 is in fluidic communication with the nasal inlet 152, thereby allowing the user to inhale from the nasal inlet 152 to the pair of nostrils. In the closed configuration, the fluidic communication between the nasal aperture 120 and the nasal inlet 152 is prevented. The nasal inhalation valve 154 is configured to assume its open configuration in response to nasal inhalation by the user, and its closed configuration in response to nasal exhalation by the user.

The respirator 100 can optionally comprises an inhalation filter 182 disposed between the nasal inlet 152 and the nasal inhalation valve 154. In some implementations, the inhalation filter 182 is disposed within the nasal fluid channel 150. In some implementations, the inhalation filter 182 is disposed at a distal end of the nasal fluid channel 150. The inhalation filter 182 is configured to filter the air entering the nasal inlet 152 (e.g., to remove pathogens, particulates, or otherwise anything undesirable to the user).

The nasal exhalation valve 156 is configured to transition between an open configuration and a closed configuration. In the open configuration, the nasal fluid channel 150 is in fluidic communication with the oral fluid channel 160 or an environment, thereby allowing the user to exhale from the pair of nostrils to the oral fluid channel 160 or the environment, or inhale with the mouth from the nasal fluid channel 150 (and by extension from the nasal fluid channel 150) to the oral fluid channel 160. In the closed configuration, air is prevented from passing through the nasal exhalation valve 156. For example, in some implementations, in the closed configuration, fluidic communication between the nasal fluid channel 150 and the oral fluid channel 160 is prevented. In some implementations, the nasal exhalation valve 156 permits nasal exhalation to combine with mouth exhalation.

The oral exhalation valve 164 is disposed within the oral fluid channel 160 between the mouth aperture 130 and the oral outlet 162. The oral exhalation valve 164 is s configured to transition between an open configuration and a closed configuration. In the open configuration, the mouth aperture 130 is in fluidic communication with the oral outlet 162. In the closed configuration, the fluidic communication between the mouth aperture 130 and the oral outlet 162 is prevented.

The respirator 100 can optionally comprise an exhalation filter 184 disposed between the oral outlet 162 and the oral exhalation valve 164. In some implementations, the exhalation filter 184 is disposed within the oral fluid channel 160. In some implementations, the exhalation filter 184 is disposed at a distal end of the oral fluid channel 160. The exhalation filter 182 is configured to filter the air exiting the oral exhalation valve 164 (e.g., to remove pathogens, particulates, or otherwise anything undesirable to the environment around the user).

The respirator 100 can optionally comprise a septum 140 disposed between the nasal fluid channel 150 and the oral fluid channel 160. The septum 140 is configured to prevent fluidic communication between the nasal fluid channel 150 and the oral fluid channel 160. In some embodiments, the septum 140 can include an obturator configured to form a seal on the face of the user to prevent fluidic communication between the nasal fluid channel 150 and the oral fluid channel 160. The nasal exhalation valve 156 can be disposed within the septum 140. While FIG. 1 only shows one optional septum, some implementations of the respirator 100 can have two, three, four, or more septa.

In some implementations, the respirator 100 further comprises a housing having an inner layer and an outer layer, and a volume defined therebetween. The housing defines the nasal inlet 152 and the oral outlet 162. The inner layer defines the nasal aperture 120 and the mouth aperture 130. The volume includes the nasal fluid channel 150 and the oral fluid channel 160, and the septum 140 is disposed between the inner layer and the outer layer to divide the volume into the nasal fluid channel 150 and the oral fluid channel 160.

In some implementations, the nasal fluid channel 150 and the oral fluid channel 160 are not divided from a common volume by a septum. Rather, each of the nasal fluid channel 150 and the oral fluid channel 160 has its independent housing defining a volume. In such implementations, the nasal aperture 120 and the mouth aperture are defined by an aperture housing 110; and the nasal fluid channel 150 and the oral fluid channel 160 can be connected to each other by the aperture housing 110, where the nasal exhalation valve 156 is disposed within the aperture housing 110 and provides fluidic communication between the nasal fluid channel 150 and the oral fluid channel 160. Further, in some such implementations, the nasal inhalation valve 154, the nasal exhalation valve 156, and the oral exhalation valve 164 are disposed within the aperture housing 110, as shown optionally in broken lines in FIG. 1. Alternatively, in some implementations, there is no fluidic communication between the nasal fluid channel 150 and the oral fluid channel 160, as the nasal exhalation valve 156 is configured to permit the user to exhale into the environment, and the respirator 100 can further comprise an oral exhalation valve configured to permit the user to exhale into the environment.

Due to its configuration, the respirator 100 permits nasal and/or oral inhalation, and nasal and/or mouth exhalation. While FIG. 1 only shows one nasal inhalation valve 154, the respirator 100 can further include one additional nasal inhalation valve, so that there is one nasal inhalation valve on each side of the nose. Similarly, while FIG. 1 only shows one oral exhalation valve 164, the respirator 100 can further include one additional oral exhalation valve, so that there is one oral exhalation valve on each side of the mouth.

In some implementations, the respirator 100 can further comprise a head mount configured to be disposed about a parietal part of the user's head and thus to provide further mechanical stability for the respirator 100. The head mount can optionally be adjustable to accommodate the different head sizes of users.

In some implementations, the respirator 100 can further comprise a coupling member (e.g., a strap) configured disposed about the cheeks of a user. In some implementations, the coupling member can optionally be adjustable to accommodate the different head sizes of users.

The inhalation filter 182 and exhalation filter 184 can operate accordingly a variety of filtering mechanisms. In some implementations, the inhalation filter 182 or the exhalation filter 184 is configured to include a liquid medium. In some implementations, the liquid medium is water or an antiseptic solution. Filtration can be achieved through a multi-stage process using various fluid properties. For example, large particles (e.g., dust, mucus, or saliva) can be removed by creating a vortex air that flows in the volume of the liquid, while finer filtering can be achieved through bubbling process when the air stream passes through a layer of unstable foam. In some implementations, the liquid medium can be replaced with a granular substance or a granular mixture, for example, activated carbon. In some embodiments, the inhalation filter 182 or the exhalation filter 184 is configured to include a roll filter. In some implementations, the inhalation filter 152 or the exhalation filter 184 is configured to include a mesh. The inhalation filter 182 or the exhalation filter 184 can be positioned horizontally or vertically, or somewhere therebetween.

Generally, the operating principle of the respirator 100 can be described as follows. When inhaling through the nose, under the influence of negative relative pressure, the nasal inhalation valve 154 opens and air enters from the nasal fluid channel 150 into the nasal aperture 120. In some implementations, the air previously passes through an inhalation filter from the space external to the respirator 100. When the user exhales through the nose, under the influence of positive relative pressure, the nasal inhalation valve 154 is closed, and the nasal exhalation valve 156 opens, and air enters the oral fluid channel 160. Under the influence of positive relative pressure, the oral exhalation valve 164 opens, and the exhaled air exits the respirator 100 through the oral outlet 162 and optionally after passing through an exhalation filter.

The outer layer of the housing is transparent, opaque, or a combination thereof (e.g., a portion of the outer layer facing the user's mouth may be transparent to aid in communication between the user and others, while other portions of the outer layer may be less transparent or opaque). The outer layer of the housing can be made of any suitable material, e.g., plastic, silicone, or the like.

The housing can be made, partially or whole, from breathable (filtering) material. In some implementations, the respirator 100 is for single use. For example, the whole housing can be made of a spunbond meltblown spunbond (SMS) material.

In some implementations, the respirator 100 is reusable. For example, a portion of the housing (e.g., the obturator) can be made of silicone and/or thermoplastic elastomer; another portion of the housing can be made of acrylonitrile butadiene styrene (ABS) plastic, or polyethylene terephthalate (PET) plastic; and valves can be made of silicone or rubber.

In some implementations, only the obturator and the coupling member (e.g., a strap) are configured to be in contact with the skin when the user wears the respirator 100. In some implementations where additional components are in contact with the skin, these additional components can be made of an air permeable material.

Regardless of whether the respirator 100 is for single use or reusable, in some implementations separate components are manufactured separately and then assembled into the respirator 100.

Figures 2C, 2D:
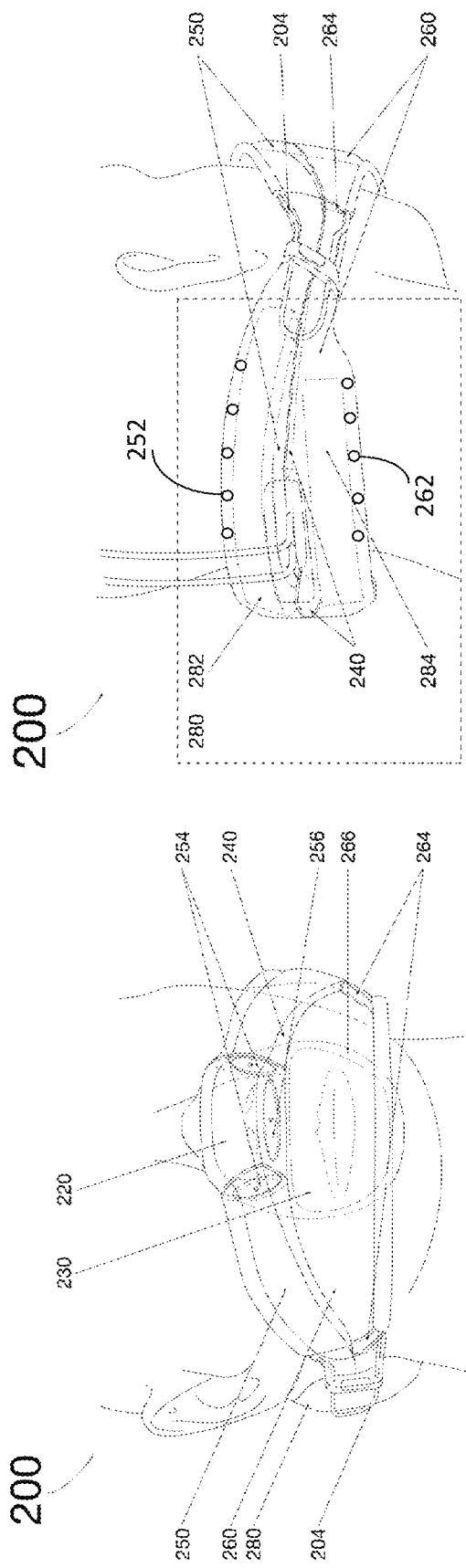
FIG. 2C is a front view of the respirator 200 of FIG. 2A.
FIG. 2D is a rear view of the respirator 200 of FIG. 2A.

FIGS. 2A-2E show different views of a respirator 200 that comprises the features of the respirator 100 shown in FIG. 1, according to an embodiment. As shown in FIG. 2A, the respirator 200 has a front-facing portion 270, a rear-facing portion 280, and a head mount 202 (in some embodiments a respirator may not include the head mount). The front-facing portion 270 is coupled to the rear-facing portion 280. The front-facing portion 270 is configured to cover the lower half of a user's face so that a nasal aperture is disposed about the nostrils of the user and a mouth aperture is disposed about the mouth of the user. The rear-facing portion 280 is configured to be disposed about the occipital part of the user's head. The head mount 202 is coupled to the rear-facing portion 280. The head mount 202 is configured to be disposed about a parietal part of the user's head and thus to provide further mechanical stability for the respirator 200.

As shown in FIG. 2C, the front-facing portion 270 of the respirator 200 comprises a nasal aperture 220, a mouth aperture 230, a septum 240, a nasal fluid channel 250, an oral fluid channel 260, two nasal inhalation valves 254, a nasal exhalation valve 256, two oral exhalation valves 264, an obturator 266, a coupling member 204, and a rear-facing portion 280.

Without reiterating the features discussed above and for the sake of brevity, the positions and functions of the nasal aperture 220, the mouth aperture 230, the septum 240, the nasal fluid channel 250, the oral fluid channel 260, the nasal inhalation valves 254, the nasal exhalation valve 256, and the oral exhalation valves 264 are the same or substantially the same as those described for the respective counterparts in the respirator 100 of FIG. 1.

The obturator 266 is disposed on the circumferences of the nasal aperture 220 and the mouth aperture 230. The obturator 266 is configured to form a seal around the nostrils and the mouth so that fluidic communication between the nasal fluid channel 250 and the oral fluid channel 260 is prevented unless the nasal exhalation valve 256 is in an open configuration.

The coupling member 204 is configured to connect the front-facing portion and the rear-facing portion 280. In some embodiments, the coupling member 204 is flexible. The coupling member 204 can optionally be adjustable to accommodate the different head sizes of users The details of the rear-facing portion 280 can be seen in FIG. 2D. Specifically, the rear-facing portion 280 comprises a housing, an inhalation filter 282, and an exhalation filter 284. The housing is configured to enclose the inhalation filter 282 and the exhalation filter 284. The inhalation filter 282 is configured to filter the inhaled air, while the exhalation filter 284 is configured to filter the exhaled air.

As shown in FIG. 2D, each of the septum 240, the nasal fluid channel 250, and the oral fluid channel 260 extends from the front-facing portion 270 to the rear-facing portion 280. The nasal inlet 252 is shown as a series of holes. The oral outlet 262 is shown as a series of holes.

Figure 2E:
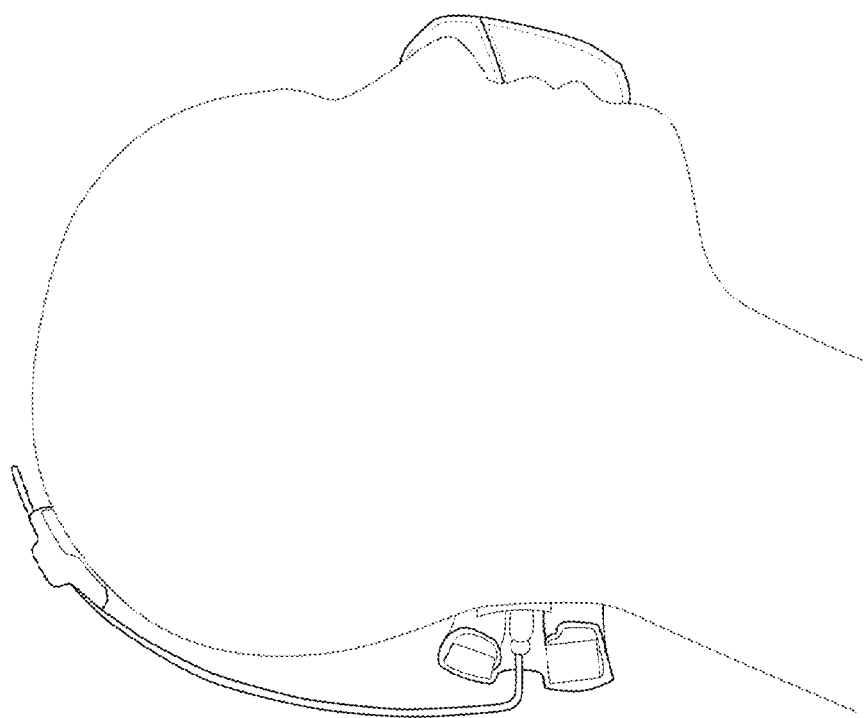
FIG. 2E is a cross-sectional view of the respirator 200 of FIG. 2A.

FIG. 2E is a cross-sectional view of the respirator 200.

Figure 2F:
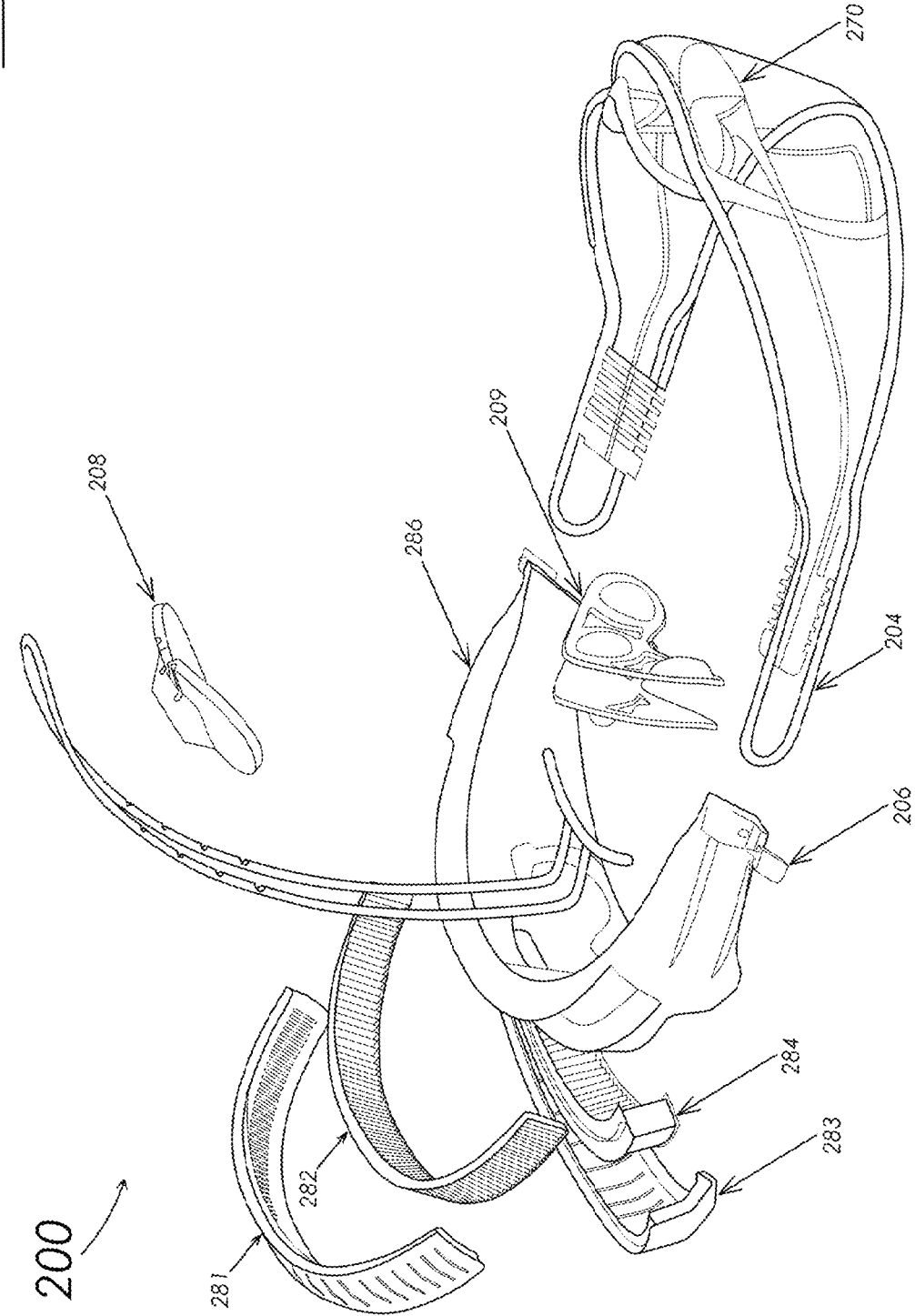
FIG. 2F is an exploded view of the respirator 200 of FIG. 2A.

FIG. 2F is an explosive view of the respirator 200. The front-facing portion 270 is coupled to a filter block 286 through the coupling member 204. A size adjuster 206 disposed on a distal end of the filter block 286 is configured to adjust the distance that the coupling member 204 can slide in so as to adjust the fitting of the front-facing portion 270 on a user's face.

The filter block 286 is configured to provide: (a) a volume for airtight installation of the filters 282 and 284; and (b) an airtight fluidic communication with the front-facing portion 270. When the filter block 286 is connected to the front-facing portion 270, a closed system is created to permit airtight flow of inhaled filtered air and exhaled filtered air for the nasal fluid channel and oral fluid channel respectively.

The inhalation filter 282 is disposed between an inhalation seal cover 281 and the filter block 286. The exhalation filter 284 is disposed between an exhalation seal cover 283 and the filter block 286. The inhalation seal cover 281 is configured to: (a) achieve an airtight press over the contour of the inhalation filter 282 to the filter block 286; and (b) provide a protective casing for the inhalation filter 282. The exhalation seal cover 283 is configured to: (a) achieve an airtight press over the contour of the exhalation filter 284 to the filter block 286; and (b) provide a protective casing for the exhalation filter 284.

The respirator 200 further comprises an attachment member 208 and an occipital support 209. When a user wears the respirator 200, the attachment member 208 is disposed on the crown of the user's head, and the occipital support 209 is disposed on the occipital part of the user's head. Both the attachment member 208 and the occipital support 209 are configured to provide mechanical stability when the user is wearing the respirator 200.

FIGS. 9A-9B show front and rear views of a respirator 900 that comprises the features of the respirator 100 shown in FIG. 1, according to an embodiment. As shown in FIGS. 9A-9B, the respirator 900 comprises an aperture housing 910, a nasal aperture 920, a mouth aperture 930, a nasal fluid channel 950, two nasal inhalation valves 954, two nasal exhalation valves 956, an oral fluid channel 960, two oral exhalation valves 964, an inhalation filter 982, and an exhalation filter 984. Note that the inhalation filter 982 and the exhalation filter 984 are installed in filter blocks.

The aperture housing 910 defines the nasal aperture 920 and the mouth aperture 930. Each of the nasal fluid channel 950 and the oral fluid channel 960 has its own housing defining a volume. The nasal fluid channel 950 is connected to the oral fluid channel 960 by the aperture housing 910.

The nasal inhalation valves 954 are disposed about the nose such that there is one nasal inhalation valve 954 on each side of the nose. The nasal exhalation valves 956 are disposed below the nostrils such that there is one nasal exhalation valve 956 below each nostril. The oral exhalation valves 964 is disposed about the mouth such that there is one oral exhalation valve 964 on each side of the mouth.

Figure 10:
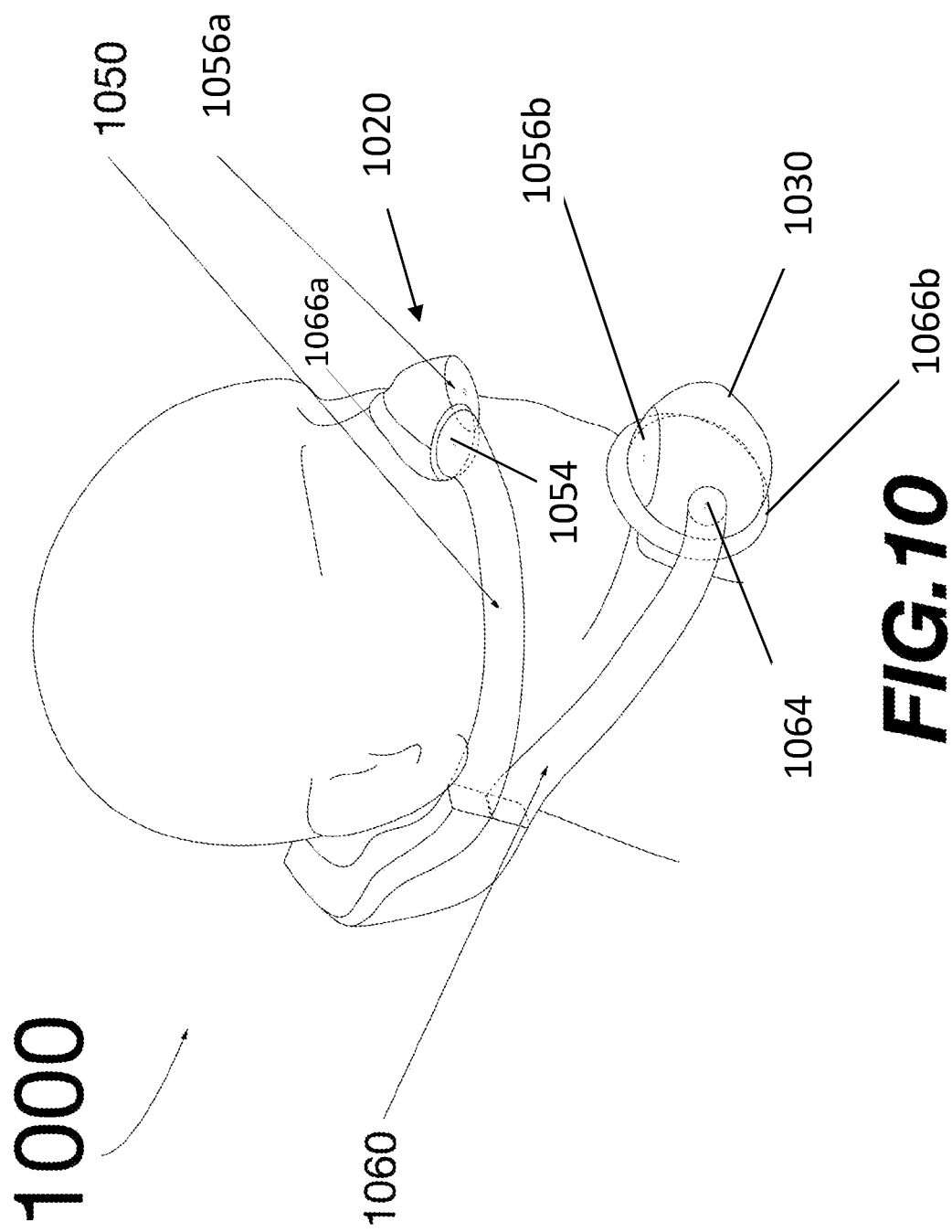
FIG. 10 is a perspective view of a respirator 1000, in accordance with an embodiment of FIG. 1.

FIG. 10 show a perspective view of a respirator 1000 that comprises the features of the respirator 100 shown in FIG. 1, according to an embodiment. The respirator 1000 comprises a nasal aperture 1020, a mouth aperture 1030, a nasal fluid channel 1050, a nasal exhalation valve having a nasal portion 1056a and an oral portion 1056b, an oral fluid channel 1060, a nasal inhalation valve 1054, and an oral exhalation valve 1064, a nasal obturator 1066a, and a mouth obturator 1066b.

The nasal portion 1056a and oral portion 1056b of the nasal exhalation valve have the same flow direction. They are connected together to form the nasal exhalation valve that permits the air to be exhaled from the nostrils to the oral fluid channel 1060. The nasal portion 1056a and oral portion 1056b can be disconnected. When they are disconnected, the nasal portion 1056a is configured to permit the user to exhale into the surrounding environment. For example, if the user decides to ingest a substance (e.g., food, drink, or a pill), the user can disconnect the nasal portion 1056a and oral portion 1056b by lowering the aperture housing for the mouth to ingest the substance, while being partially protected by inhalation through the nose and exhalation into the surrounding environment.

The nasal obturator 1066a is disposed on the circumferences of the nasal aperture 1020. The nasal obturator 1066a is configured to form a seal around the nostrils. The mouth obturator 1066b is disposed on the circumferences of the mouth aperture 1030. The mouth obturator 1066b is configured to form a seal around the mouth.

Figure 3:
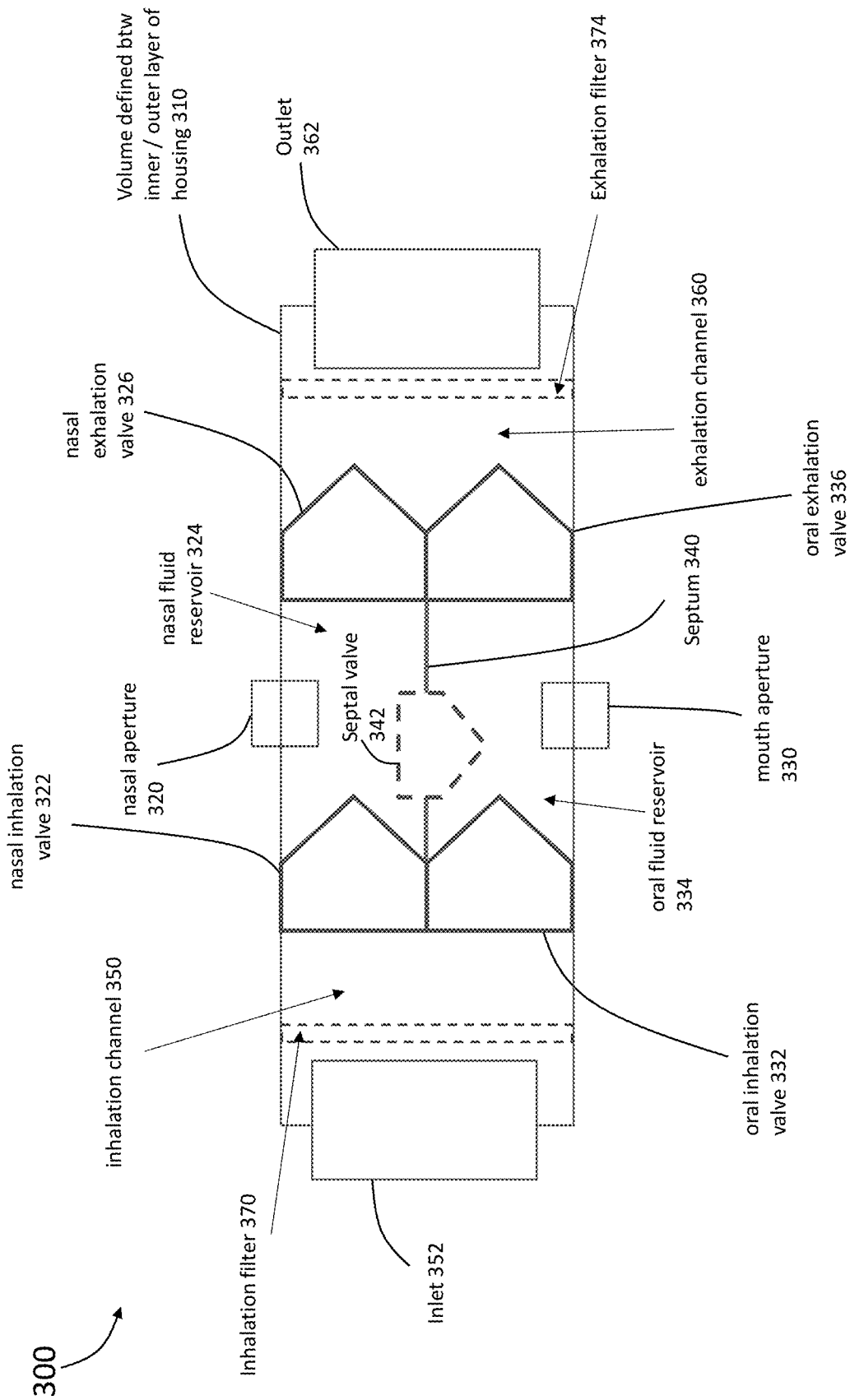
FIG. 3 is a schematic diagram illustrating a respirator 300, in accordance with an embodiment.

FIG. 3 shows an embodiment of a respirator 300 where inhalation can be done through the nose or mouth, each through a separate valve, and exhalation can also be done through the nose or mouth, each through a separate value. The inhaled air shares a common pathway, and the exhaled air shares a common pathway.

The respirator 300 comprises: (a) a housing having an inner layer and an outer layer defining volume 310 therebetween, (b) a nasal aperture 320, (c) a nasal inhalation valve 322, (d) a nasal fluid reservoir 324, (e) a nasal exhalation valve 326, (f) a mouth aperture 330, (g) an oral inhalation valve 332, (h) an oral fluid reservoir 334, (i) an oral exhalation valve 336, (j) a septum 340, (k) an inhalation channel 350, (l) an inhalation inlet 352, (m) an exhalation channel 360, and (n) an exhalation outlet 362.

The nasal aperture 320 is defined by the inner layer and configured to be disposed about a pair of nostrils of a user. The mouth aperture 330 is defined by the inner layer and configured to be disposed about a mouth of the user when the nasal aperture 320 is disposed about the nostrils of the user.

The respirator 300 can further comprise an obturator (not shown) disposed on the circumferences of the nasal aperture 120 and the mouth aperture 130. The obturator is configured to form a seal around the nostrils and the mouth so that fluidic communication between the inhalation channel 350 and the exhalation channel 360 is prevented unless at least one of the inhalation or exhalation valves (322, 326, 332, 336) is in an open configuration.

The septum 340 is disposed between the inner layer and the outer layer and divides the volume 310 into the nasal fluid reservoir 324 and the oral fluid reservoir 334. The septum 340 is configured to prevent fluidic communication between the nasal fluid reservoir 324 and the oral fluid reservoir 334. The nasal fluid reservoir 324 is configured to be in fluidic communication with the pair of nostrils. The oral fluid reservoir 334 is configured to be in fluidic communication with the mouth of the user. In some embodiments, the septum 340 can include an obturator configured to form a seal on the face of the user to prevent fluidic communication between the nasal fluid reservoir 324 and the mouth fluid reservoir 334.

The nasal inhalation valve 322 is disposed between the nasal fluid reservoir 324 and the inhalation channel 350 that is in fluidic communication with the inhalation inlet 352. The nasal inhalation valve 322 is configured to transition between an open configuration and a closed configuration. In the open configuration, the nasal fluid reservoir 324 is in fluidic communication with the inhalation channel 350, and by extension, the inhalation inlet 352. In the closed configuration, fluidic communication between the nasal fluid reservoir 324 and the inhalation channel 350, and by extension, the inhalation inlet 352, is prevented. The nasal inhalation valve 322 is configured to assume its open configuration in response to nasal inhalation by the user, and its closed configuration in response to nasal exhalation by the user, as described in more detail below.

The nasal exhalation valve 326 is disposed between the nasal fluid reservoir 324 and the exhalation channel 360 that is in fluidic communication with the exhalation outlet 362. The nasal exhalation valve 326 is configured to transition between an open configuration and a closed configuration. In the open configuration, the nasal fluid reservoir 324 is in fluidic communication with the exhalation channel 360, and by extension the exhalation outlet 362. In the closed configuration, fluidic communication between the nasal fluid reservoir 324 and the exhalation channel 360, and by extension, the exhalation outlet 362, is prevented. The nasal exhalation valve 326 is configured to assume its open configuration in response to nasal exhalation by the user, and its closed configuration in response to nasal inhalation by the user.

The oral inhalation valve 332 is disposed between the oral fluid reservoir 334 and the inhalation channel 350 that is in fluidic communication with the inhalation inlet 352. The oral inhalation valve 332 is configured to transition between an open configuration and a closed configuration. In the open configuration, the oral fluid reservoir 334 is in fluidic communication with the inhalation channel 350, and by extension, the inhalation inlet 352. In the closed configuration, fluidic communication between the oral fluid reservoir 334 and the inhalation channel 350, and by extension, the inhalation inlet 352, is prevented. The oral inhalation valve 332 is configured to assume its open configuration in response to oral inhalation by the user, and its closed configuration in response to oral exhalation by the user.

The oral exhalation valve 336 is disposed between the oral fluid reservoir 334 and the exhalation channel 360 that is in fluidic communication with the exhalation outlet 362. The oral exhalation valve 336 is configured to transition between an open configuration and a closed configuration. In the open configuration, the oral fluid reservoir 334 is in fluidic communication with the exhalation channel 360, and by extension, the exhalation outlet 362. In the closed configuration, fluidic communication between the oral fluid reservoir 334 and the exhalation channel 360, and by extension, the exhalation outlet 362, is prevented. The oral exhalation valve 336 is configured to assume its open configuration in response to oral exhalation by the user, and its closed configuration in response to oral inhalation by the user.

In some implementations, the respirator 300 further comprises an inhalation filter 370 disposed between (1) the inhalation inlet 352 and (2) the nasal inhalation valve 322 and the oral inhalation valve 332. In some implementations, the inhalation filter 370 is disposed within the inhalation channel 350. In some implementations, the inhalation filter 370 is disposed at a distal end of the inhalation channel 350. The inhalation filter 370 is configured to filter the air entering the inhalation inlet 352 (e.g., to remove pathogens, particulates, or otherwise anything undesirable to the user).

The respirator 300 can optionally comprise an exhalation filter 374 disposed between (1) the exhalation outlet 362 and (2) the nasal exhalation valve 326 and the oral exhalation valve 336. In some implementations, the exhalation filter 374 is disposed within the exhalation channel 360. In some implementations, the exhalation filter 374 is disposed at a distal end of the exhalation channel 360. The exhalation filter 374 is configured to filter the air exiting the nasal exhalation valve 326 or the oral exhalation valve 336 (e.g., to remove pathogens, particulates, or otherwise anything undesirable to the environment around the user).

The inhalation filter 370 and exhalation filter 374 can operate accordingly a variety of filtering mechanisms. In some implementations, the inhalation filter 370 or the exhalation filter 374 is configured to include a liquid medium. In some implementations, the liquid medium is water or an antiseptic solution. Filtration can be achieved through a multi-stage process using various fluid properties. For example, large particles (e.g., dust, mucus, or saliva) can be removed by creating a vortex air that flows in the volume of the liquid, while finer filtering can be achieved through bubbling process when the air stream passes through a layer of unstable foam. In some implementations, the liquid medium can be replaced with a granular substance or a granular mixture, for example, activated carbon. In some implementations, the inhalation filter 370 or the exhalation filter 374 is configured to include a roll filter. In some implementations, the inhalation filter 370 or the exhalation filter 374 is configured to include a mesh. The inhalation filter 370 or the exhalation filter 374 can be positioned horizontally or vertically, or somewhere therebetween.

In some implementations, the respirator 300 further comprises a septal valve 342 disposed within the septum and configured to transition between an open configuration and a closed configuration. In the open configuration, the nasal fluid reservoir 324 is in fluidic communication with the oral fluid reservoir 334. In the closed configuration, fluidic communication between the nasal fluid reservoir 324 and the oral fluid reservoir 334 is prevented. The septal valve 342 is configured to assume its open configuration in response to oral inhalation or nasal exhalation by the user, and its closed configuration in response to oral exhalation or nasal inhalation by the user.

While FIG. 3 only shows one septum, some implementations of the respirator 300 can have two, three, four, or more septa. While FIG. 3 only shows one optional septal valve, some implementations of the respirator 300 can have two, three, four, or more septal valves. While FIG. 3 only shows one nasal inhalation valve, some implementations of the respirator 300 can have two, three, four, or more nasal inhalation valves. While FIG. 3 only shows one nasal exhalation valve, some implementations of the respirator 300 can have two, three, four, or more nasal exhalation valves. While FIG. 3 only shows one oral inhalation valve, some implementations of the respirator 300 can have two, three, four, or more oral inhalation valves. While FIG. 3 only shows one oral exhalation valve, some implementations of the respirator 300 can have two, three, four, or more oral exhalation valves.

Generally, the operating principle of the respirator 300 can be described as follows. When inhaling through the nose or mouth, under the influence of negative relative pressure, the nasal inhalation valve 322 or the oral inhalation valve 332 opens, and air enters from the inhalation channel 350 into the nasal fluid reservoir 324 or the oral fluid reservoir 334. The air previously passes through an optional inhalation filter (not shown) from the space external to the respirator 300. When the user exhales through the nose or mouth, under the influence of positive relative pressure, the nasal inhalation valve 322 or the oral inhalation valve 332 is closed, and the nasal exhalation valve 326 or the oral exhalation valve 336 opens, and air enters the exhalation channel 360. The exhaled air exits the respirator 300 through the outlet 362 and optionally after passing through an exhalation filter (not shown).

The outer layer of the housing is transparent, opaque, or a combination thereof (e.g., a portion of the outer layer facing the user's mouth may be transparent to aid in communication between the user and others, while other portions of the outer layer may be less transparent or opaque). The outer layer of the housing can be made of any suitable material, e.g., plastic, silicone, or the like.

The housing can be made, partially or whole, from breathable (filtering) material. In some implementations, the respirator 300 is for single use. For example, the whole housing can be made of a spunbond meltblown spunbond (SMS) material.

In some implementations, the respirator 300 is reusable. For example, a portion of the housing (e.g., the obturator) can be made of silicone and/or thermoplastic elastomer; another portion of the housing can be made of ABS plastic, or polyethylene terephthalate (PET) plastic; and valves can be made of silicone or rubber.

In some implementations, only the obturator and the coupling member (e.g., a strap) are configured to be in contact with the skin when the user wears the respirator 300. In some implementations where additional components are in contact with the skin, these additional components can be made of an air permeable material.

Regardless of whether the respirator 300 is for single use or reusable, in some implementations separate components are manufactured separately and then assembled into the respirator 300.

Figure 4A:
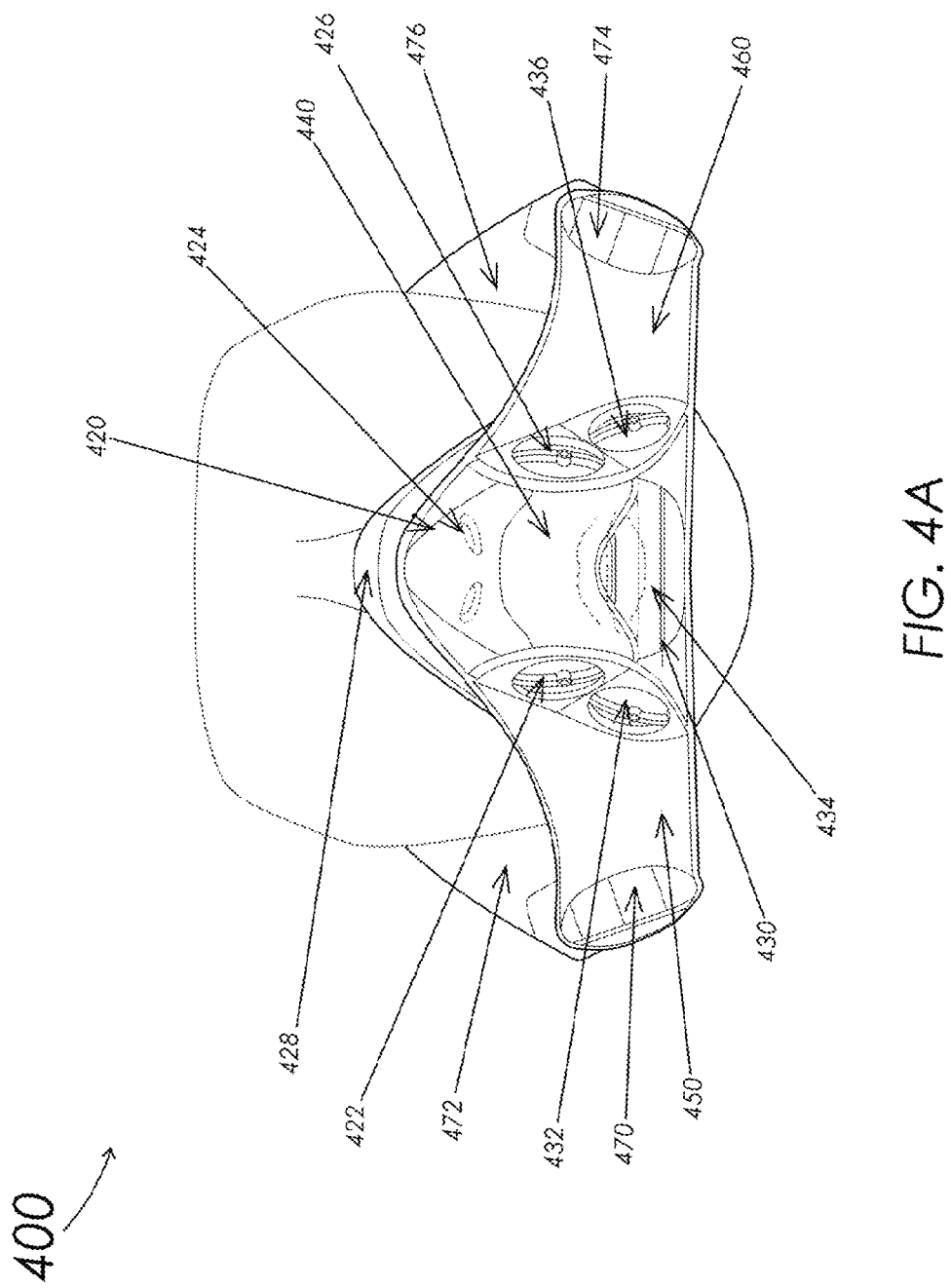
FIG. 4A is a front view of a respirator 400, in accordance with an embodiment of FIG. 3.

The respirator 400 of FIG. 4A has features consistent with the schematic diagram of FIG. 3, according to an embodiment. The respirator 400 comprises a nasal aperture 420, a nasal fluid reservoir 424, a nasal inhalation valve 422, a nasal exhalation valve 426, an obturator 428, a mouth aperture 430, an oral fluid reservoir 434, an oral inhalation valve 432, an oral exhalation valve 436, a septum 440, an inhalation channel 450, an exhalation channel 460, an inhalation filter 470, an inspiratory filter unit 472, an exhalation filter 474, and an expiratory filter unit 476.

Without reiterating the features discussed above and for the sake of brevity, the positions and functions of the nasal aperture 420, the nasal fluid reservoir 424, the nasal inhalation valve 422, the nasal exhalation valve 426, the mouth aperture 430, the oral fluid reservoir 434, the oral inhalation valve 432, the oral exhalation valve 436, the septum 440, the inhalation channel 450, and the exhalation channel 460 are the same or substantially the same as those described for the respective counterparts in the respirator 300 of FIG. 3.

The obturator 428 is disposed on the circumferences of the nasal aperture 420 and the mouth aperture. The obturator 428 is configured to form a seal around nostrils and the mouth so that fluidic communication between the nasal fluid reservoir and the oral fluid reservoir is prevented.

The inhalation filter 470 is disposed between the inhalation inlet and the nasal inhalation valve 422. The inhalation filter 470 is configured to filter the inhaled air. The exhalation filter 474 is disposed between the nasal exhalation valve 426 and the exhalation outlet. The exhalation filter is configured to filter the exhaled air.

The inhalation inlet 452 is shown as a series of holes in FIG. 4D. The exhalation outlet 462 is shown as a series of holes in FIG. 4D.

Figure 4B:
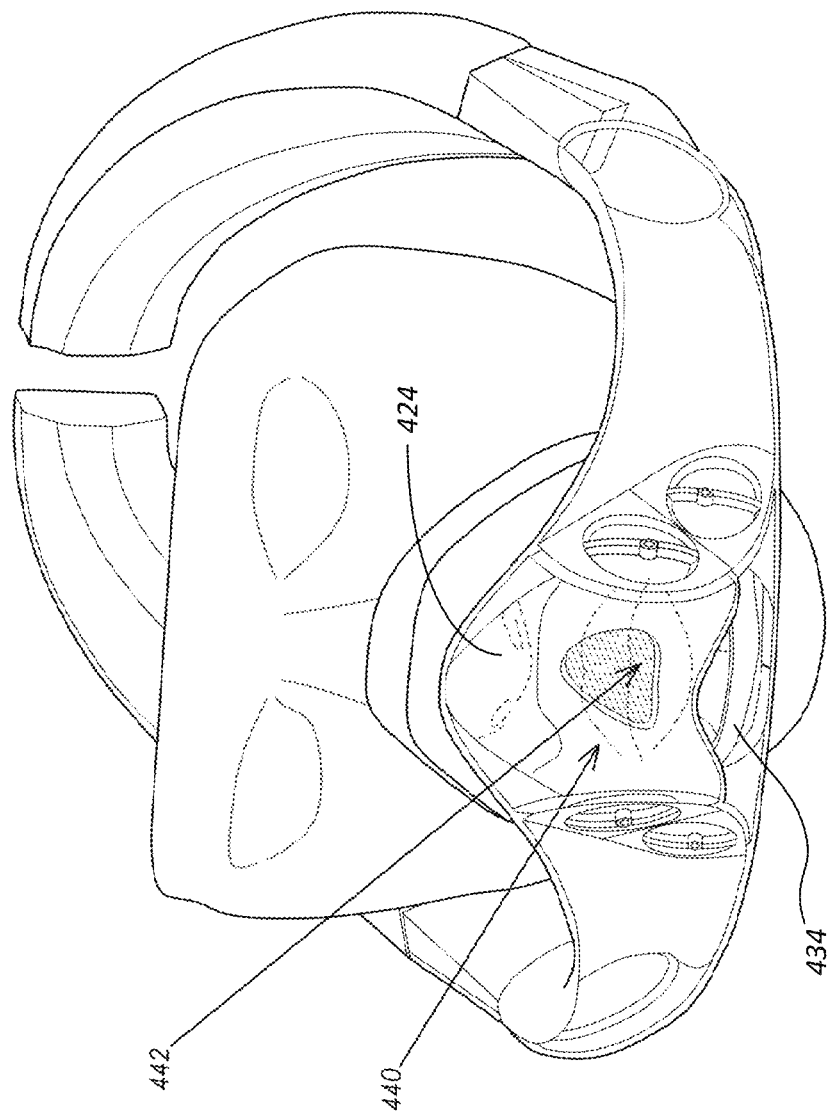
FIG. 4B is a front view of the respirator 400 with an inhalation valve 442 disposed within the septum 440.
Figure 4E:
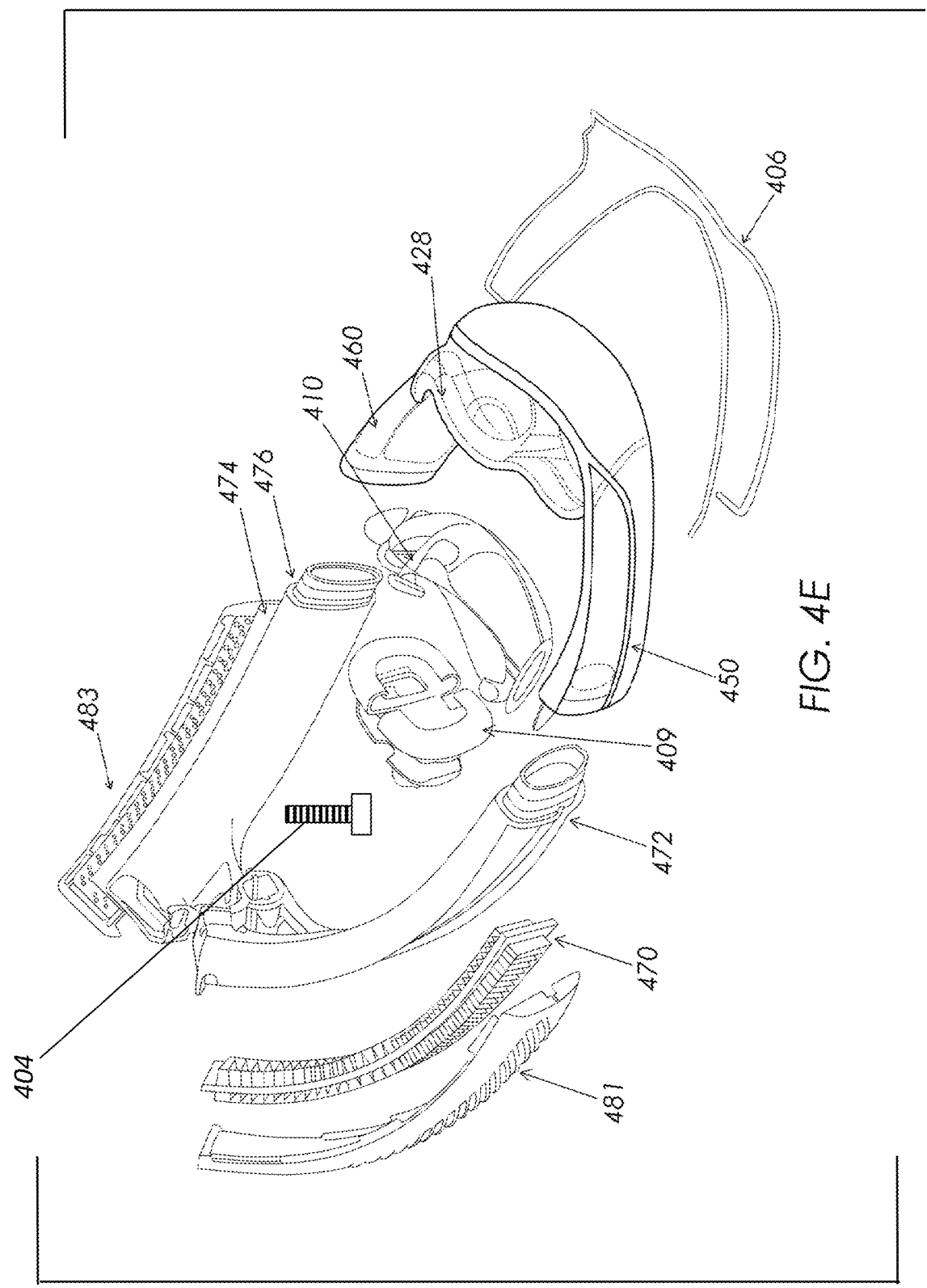
FIG. 4E is an explosive view of the respirator 400.

FIG. 4E is an explosive view of the respirator 400. In this view, the physical relationships between the inhalation filter 470 and the inspiratory filter unit 472, and between the exhalation filter 474 and the expiratory filter unit 476 are more easily understood. The inhalation filter 470 is disposed between the inhalation seal cover 481 and the inspiratory filter unit 472. The exhalation filter 474 is disposed between the exhalation seal cover 483 and the expiratory filter unit 476.

The inspiratory filter unit 472 is configured to provide: (a) a volume for airtight installation of the inhalation filter 470; and (b) an airtight fluidic communication with the inhalation channel 450. When the inspiratory filter unit 472 is connected to the inhalation channel, a closed system is created to permit airtight flow of inhaled filtered air.

The inhalation seal cover 481 is configured to: (a) achieve an airtight press over the contour of the inhalation filter 470 to the inspiratory filter unit 472; and (b) provide a protective casing for the inhalation filter 470.

The expiratory filter unit 476 is configured to provide: (a) a volume for airtight installation of the exhalation filter 474; and (b) an airtight fluidic communication with the exhalation channel 460. When the expiratory filter unit 476 is connected to the exhalation channel, a closed system is created to permit airtight flow of exhaled filtered air.

The exhalation seal cover 483 is configured to: (a) achieve an airtight press over the contour of the exhalation filter 474 to the expiratory filter unit 476; and (b) provide a protective casing for the exhalation filter 474.

In FIG. 4E, the first coupling member 404, the second coupling member 406, the occipital support 409, the aperture housing 410, and the obturator 428 are also shown. The first coupling member 404 is configured to lock the inspiratory filter unit 472 and the expiratory filter unit 476 together. The second coupling member 406 is configured to couple: (a) the inhalation channel 450 with the inspiratory filter unit 472; and (b) the exhalation channel 460 with the expiratory filter unit 476. The occipital support 409 is configured to be disposed on the occipital part of a user's head and provide mechanical stability when the user wears the respirator 400.

Figure 4F:
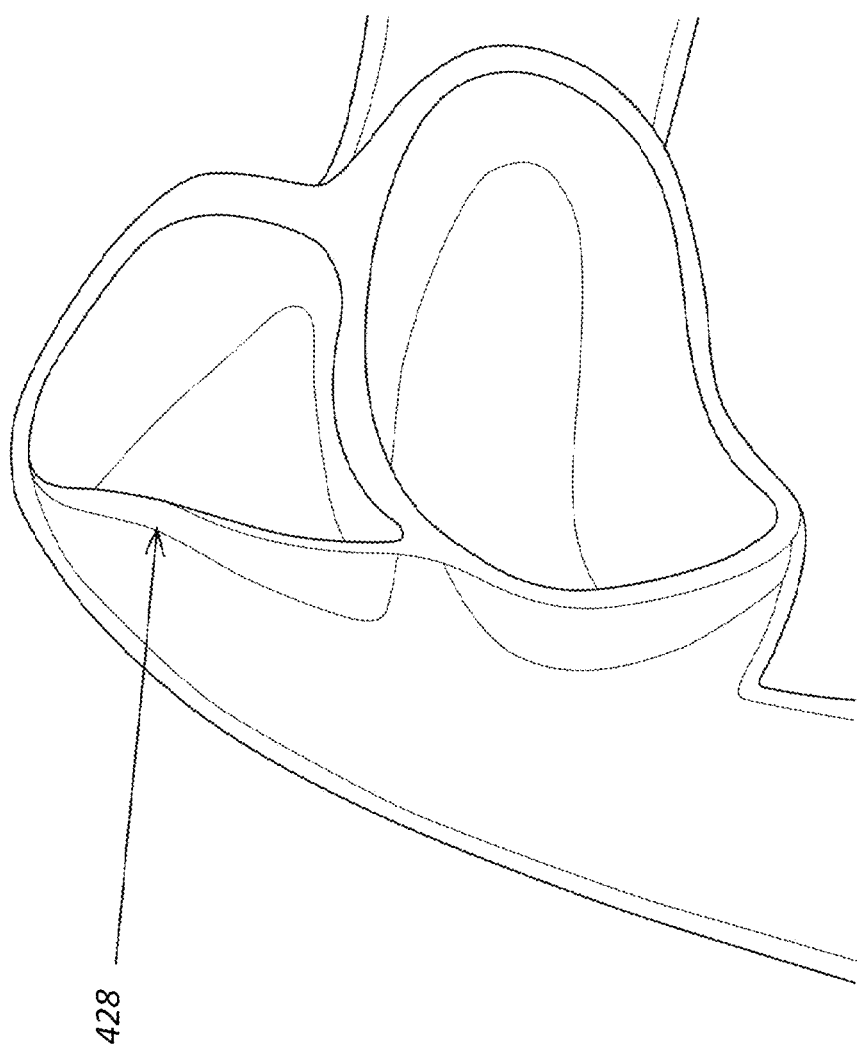
FIG. 4F is a close-up view of the obturator shown in FIG. 4E.

FIG. 4F is a close-up view of the obturator 428 shown in FIG. 4E. The obturator 428 is configured to: (a) be disposed on the circumferences of the nasal aperture and the mouth aperture; and (b) form a seal around the nostrils and the mouth.

FIG. 4B additionally comprises a second oral inhalation valve 442 as compared to the respirator in FIG. 4A. The second oral inhalation valve 442 is disposed within the septum 440. The second oral inhalation valve 442 is configured to transition between an open configuration and a closed configuration. In the open configuration, the oral fluid reservoir 434 is in fluidic communication with the nasal fluid reservoir 424, and by extension, the inhalation inlet (not shown). In the closed configuration, fluidic communication between the oral fluid reservoir 434 and the nasal fluid reservoir 424, and by extension, the inhalation inlet, is prevented. The second oral inhalation valve 442 is configured to assume its open configuration in response to oral inhalation by the user, and its closed configuration in response to oral exhalation by the user. The second oral inhalation valve 442 can thus increase the breathing capacity by at least twice. In some implementations, the opening pressure required for opening the second oral inhalation valve 442 is greater than that for the oral inhalation valve 432, thereby restricting the use of the second oral inhalation valve 442 to more intense oral inhalation, e.g., during exercising.

Figure 4I:
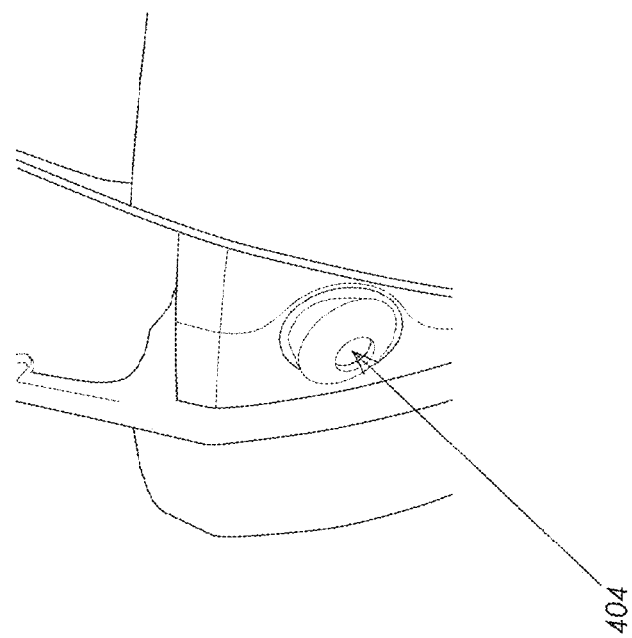
FIGS. 4G-4I show open-type frame mechanisms for securing the respirator 400 on a user's head.
Figure 4H:
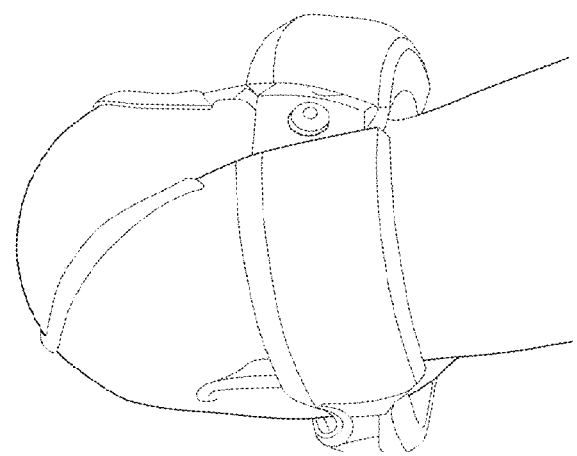
Figure 4G:
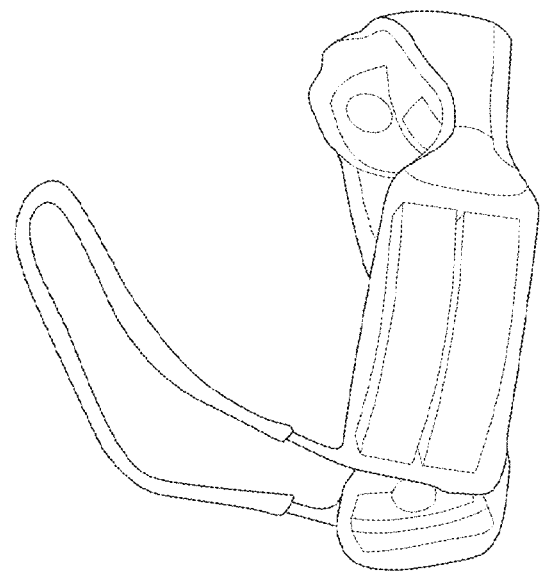
Figure 4K:
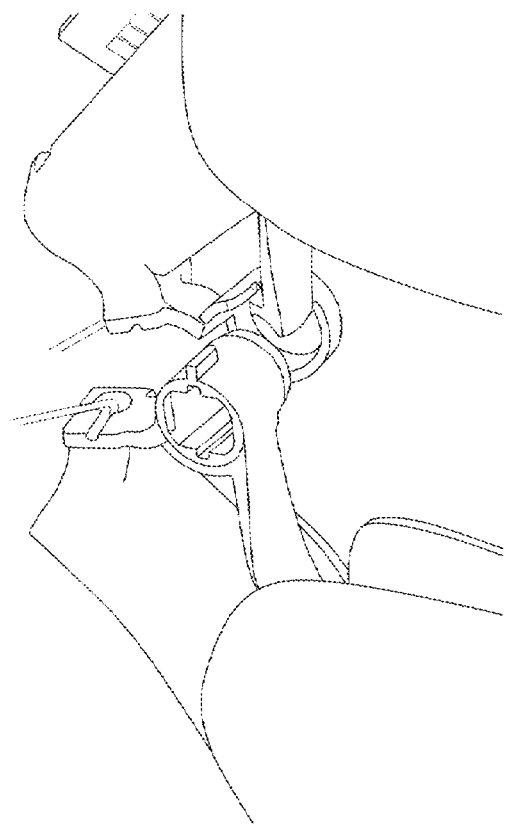
FIGS. 4J-4K depict a mechanism for opening the frame of the respirator 400.
Figure 4J:
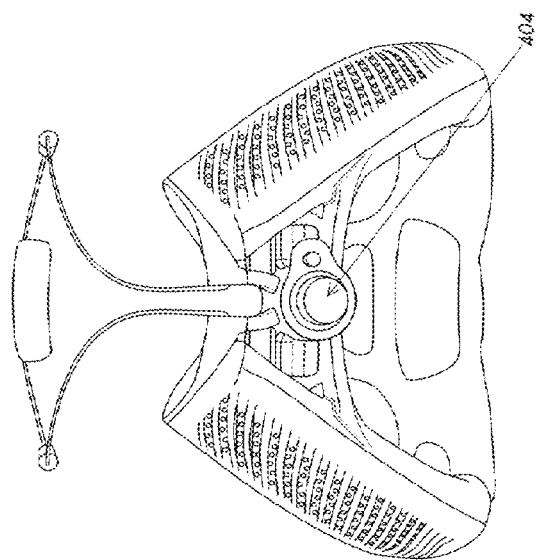

The respirator 400 can be secured to the head of a user through an open-type frame mechanism. For the convenience of putting on a respirator, each filter can be made of two or more parts, so that it can be opened. In this case, the attachment for the crown of the head can be made in the form of a ring or half ring or any appropriate form complimentary to user's head anatomy. The parts of each filter can be closed using any suitable mechanism, such as, for example, magnets, zip ties, glue, mechanical locks, snap fits, interference fits, hook and loop fasteners, etc. At the same time, each half of each filter has its own inhalation and exhalation filter (in the case of horizontal division of the internal cavity of the respirator frame). FIGS. 4G-4I show the open-type frame mechanisms. As shown in FIGS. 4I-4K, a coupling member (e.g., a button, a screw, etc.) 404 can be used to lock the inspiratory filter unit and the expiratory filter unit together. By removing the coupling member, the inspiratory filter unit and expiratory filter unit are decoupled from each other, thereby permitting the user to remove the respirator.

Figure 5A:
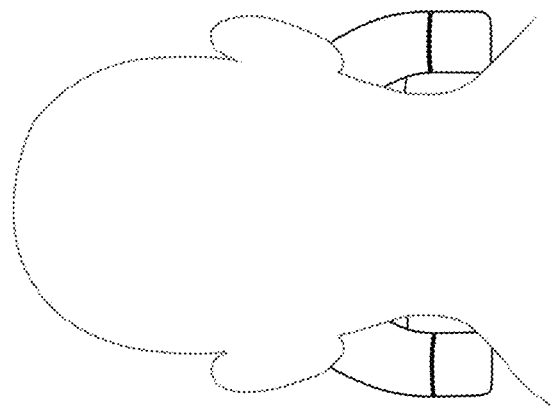
FIGS. 5A-5C are illustrations showing three different view of a respirator 500, in accordance with an embodiment of FIG. 3.
Figure 5B:
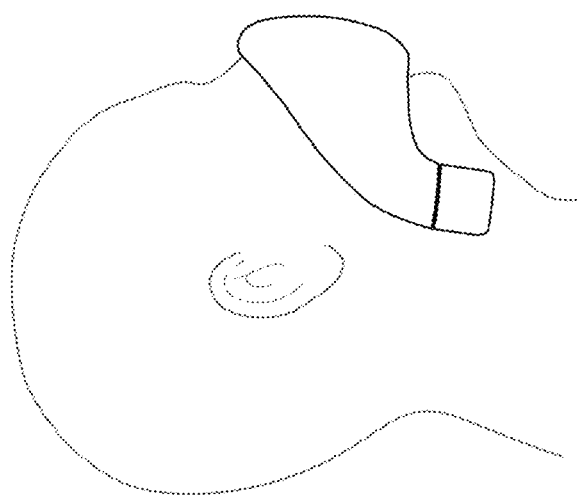
Figure 5C:
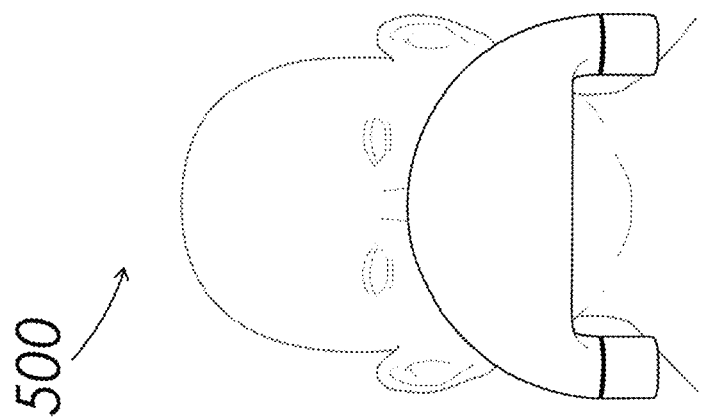
Figure 5D:
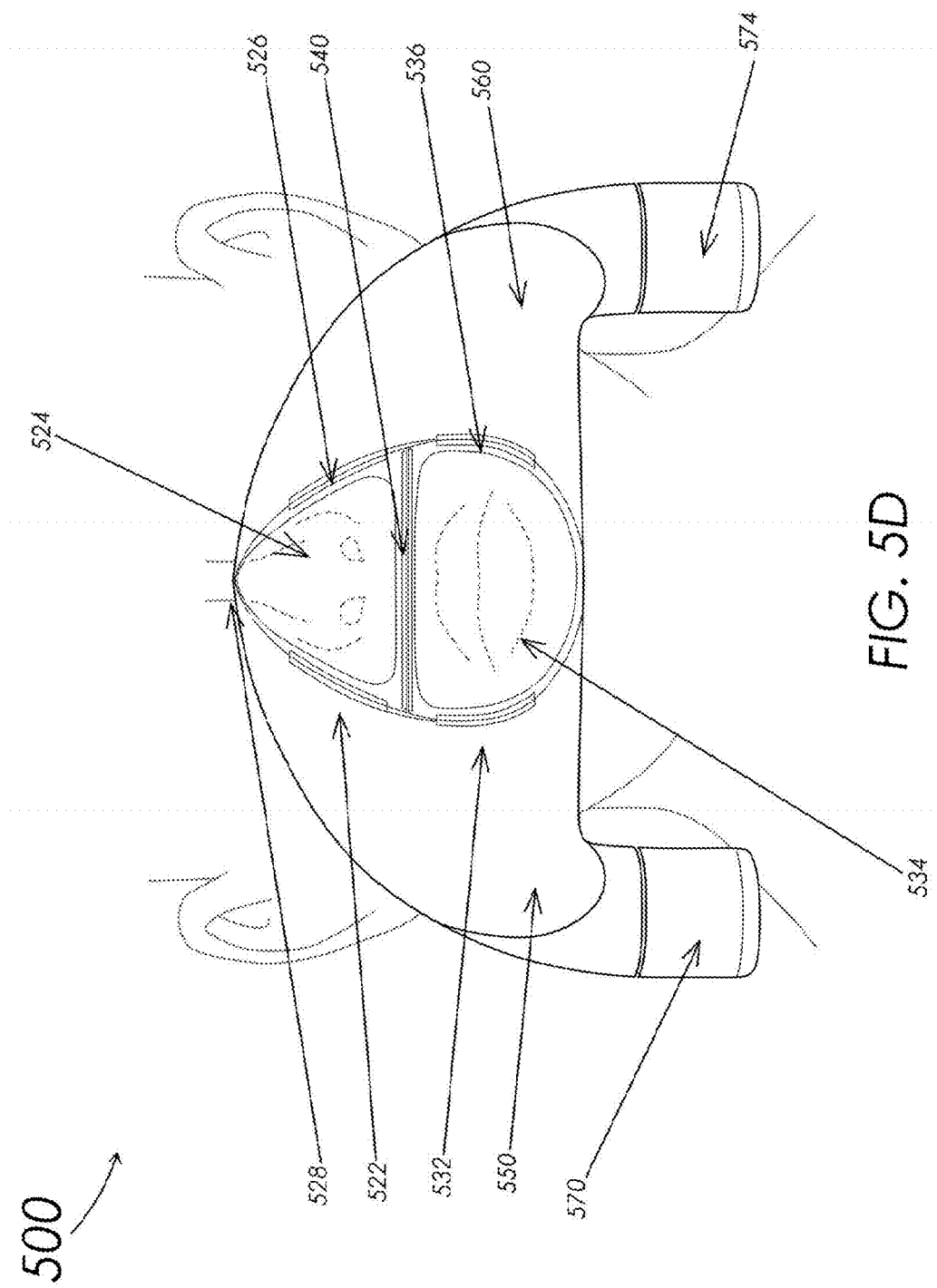
FIG. 5D is an illustration of the respirator 500 where the outer wall is made transparent.
Figure 5F:
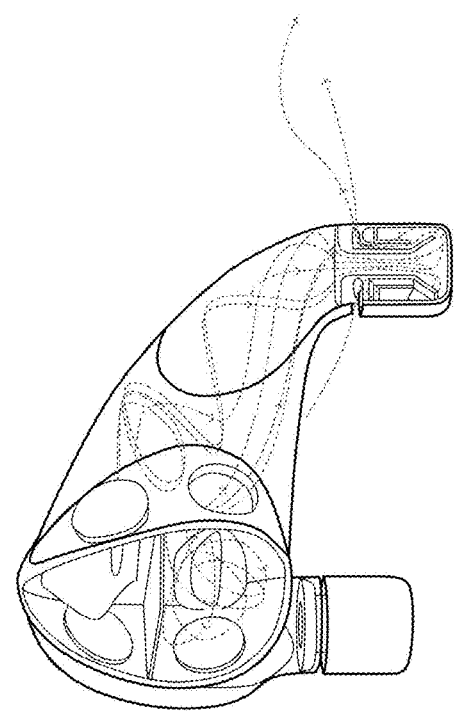
FIG. 5F is an illustration showing the air flow when exhaling through the mouth.
Figure 5E:
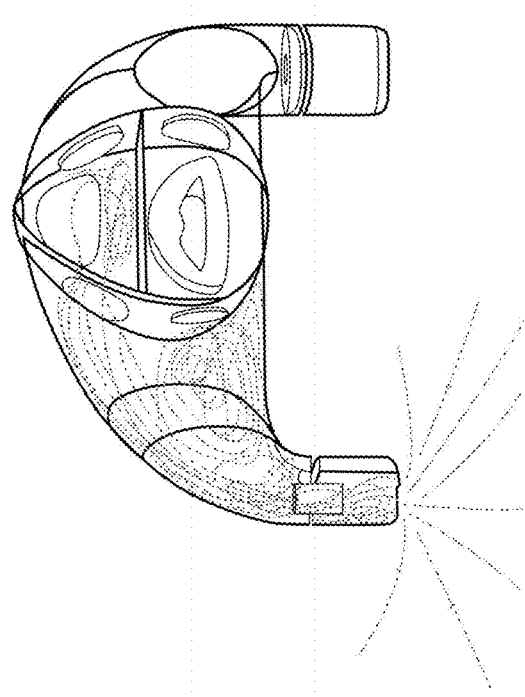
FIG. 5E is an illustration showing the air flow when inhaling through the nose.

FIGS. 5A-5F show a respirator 500 that does not have a rear-facing portion. The respirator 500 of has features consistent with the schematic diagram of FIG. 3, according to an embodiment. As shown in FIG. 5D, the respirator 500 comprises a nasal fluid reservoir 524, a nasal inhalation valve 522, a nasal exhalation valve 526, an obturator 528, an oral fluid reservoir 534, an oral inhalation valve 532, an oral exhalation valve 536, a septum 540, an inhalation channel 550, an exhalation channel 560, an inhalation filter 570, and an exhalation filter 574.

Figure 5G:
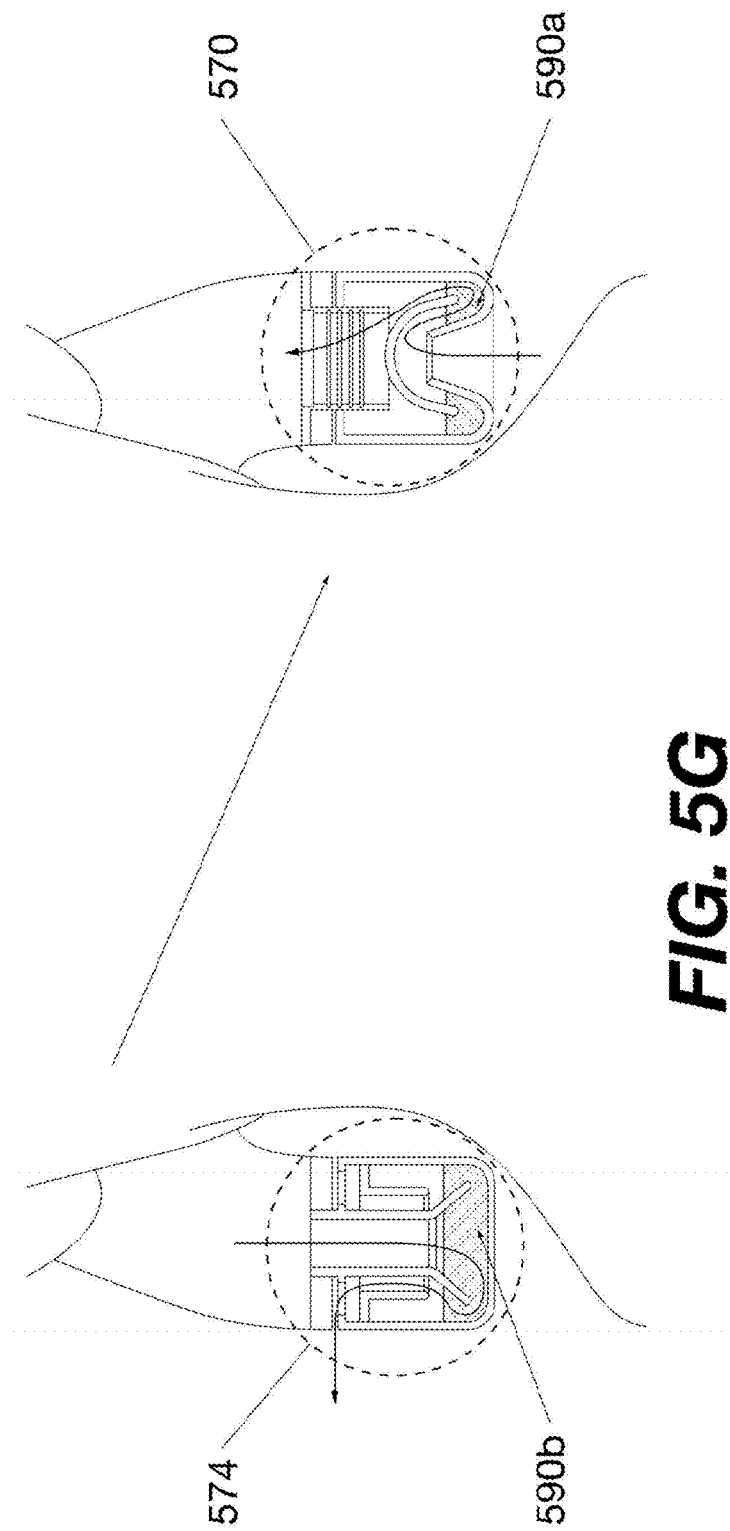
FIG. 5G is a cross-sectional view of a filter device with liquid media 590a and 590b, the right arrow shows the filtration pathway for inhalation, and the left arrow shows the filtration pathway for exhalation.

FIG. 5G shows an inhalation filter 570 and an exhalation filter 574 each having a liquid medium 590a and 590b respectively for filtration purposes. The inhalation filter 570 and exhalation filter 574 comprise structures that force the air to pass through the liquid medium 590a and 590b when the air passes from the inlet to the outlet. The inhalation filter 570 is shown on the right-hand side of FIG. 5G, where the arrow illustrates the filtration pathway as the air enters and exits the inhalation filter 570. The liquid medium 590a is disposed on the bottom of the inhalation filter 570. As the inhaled air flows through the liquid medium 590a, the inhaled air gets filtered. The exhalation filter 574 is shown on the left-hand side of FIG. 5G, wherein the arrow illustrates the filtration pathway as the air enters and exists the exhalation filter 574. The liquid medium 590b is disposed on the bottom of the exhalation filter 574. As the exhaled air flows through the liquid medium 590b, the exhaled air gets filtered.

If the filter housing is made of transparent materials, it will be possible to visually determine the degree of contamination of the liquid medium and promptly make a decision if washing and refueling with a fresh liquid medium are needed. In addition, a colorographic or numeric chart can be used to determine the rate of contamination of the filter and the remaining time of use, based on the transparency of the liquid.

Figure 5I:
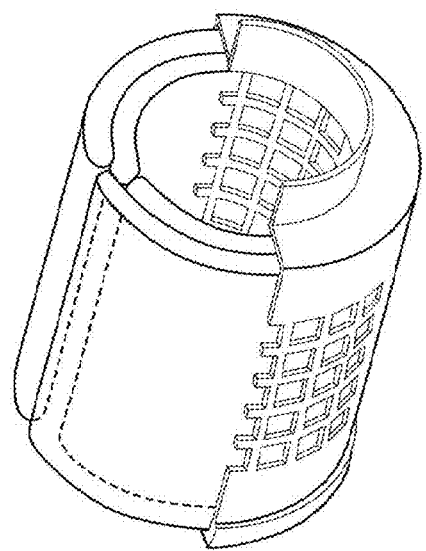
FIG. 5I is an illustration of a roll filter.
Figure 5H:
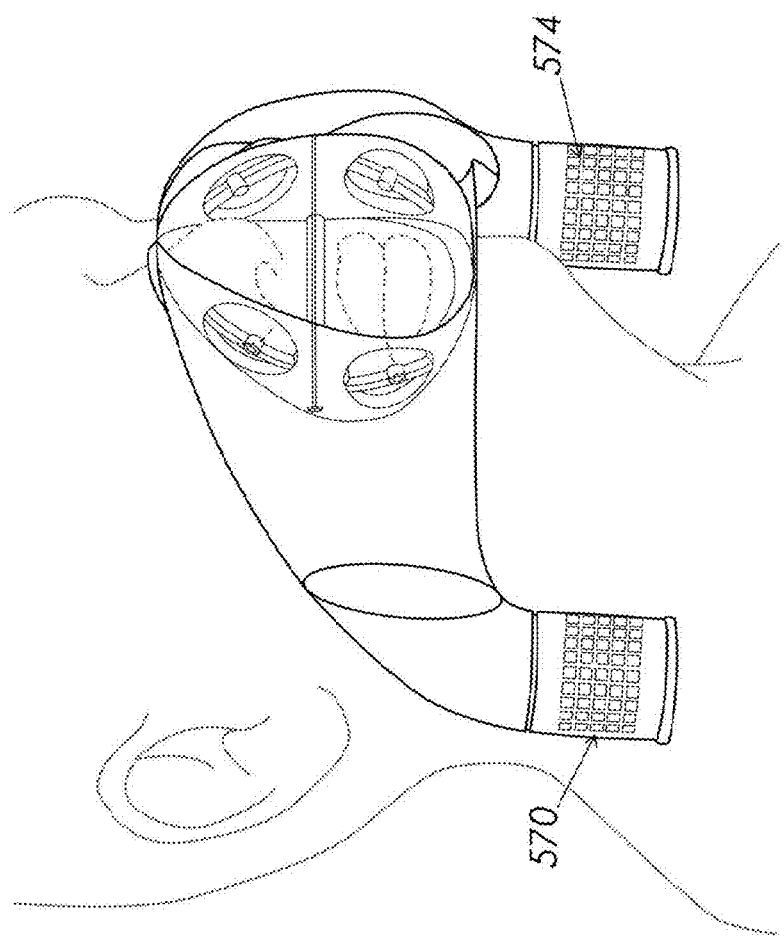
FIG. 5H is an illustration showing a filter device with a roll filter.

In some embodiments, instead of a liquid medium, a roll filter can be used for either the inhalation filter, the exhalation filter, or both. For example, FIG. 5H is an illustration showing an inhalation filter 570 and an exhalation filter 574 each having a roll filter disposed therein. In the roll filter shown in FIGS. 5H and 5I, the air flow moves across the filter material. The filter material can be arranged horizontally rather than vertically, in some implementations. The respirator case itself can have multiple walls, forming a cavity in which the filter material is located.

In some embodiments, instead of a liquid medium, a granular substance or a granular mixture, for example activated carbon, can be used as a filter material.

There are conditions, when while using RPD's there's no need to filter the exhaled air, for example, when performing construction. At the same time, the filter capacity (i.e., the ability to accumulate and retain pollutants) should be significantly higher than that of a civilian hydro-respirator. As shown in the industrial respirator 600 of FIGS. 6A-6D, the inhaled air, through the nose and/or mouth, passes through an inhalation filter, and the exhaled air leaves freely, without filtration. The respirator 600 comprises the features of the respirator 100 shown in FIG. 1 except that the respirator 600 does not have an exhalation filter, according to an embodiment.

Figure 6C:
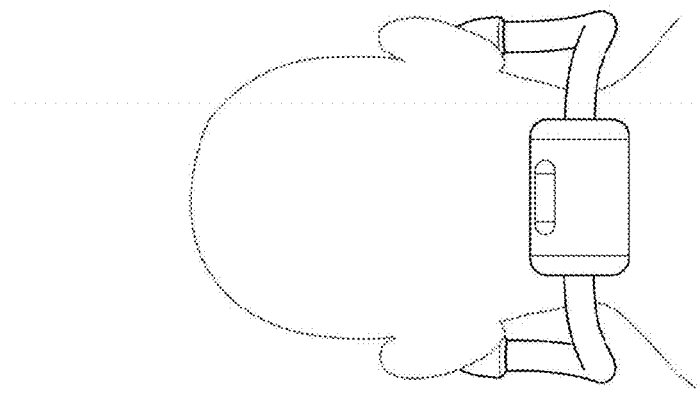
FIGS. 6A-6C are illustrations showing three different view of an industrial respirator 600, in accordance with an embodiment.
Figure 6B:
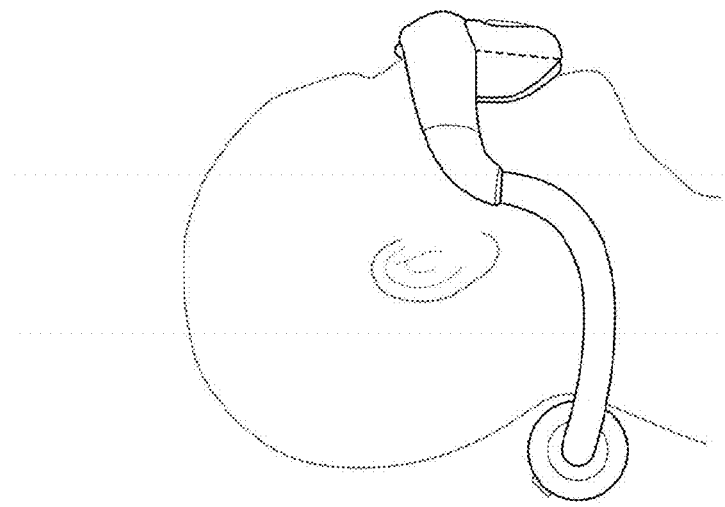
Figure 6A:
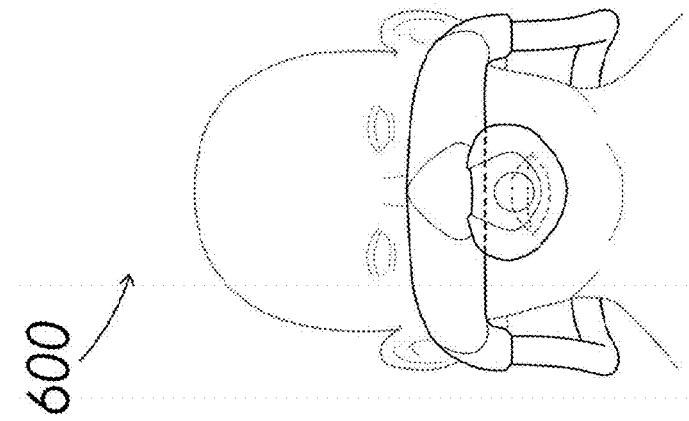
Figure 6D:
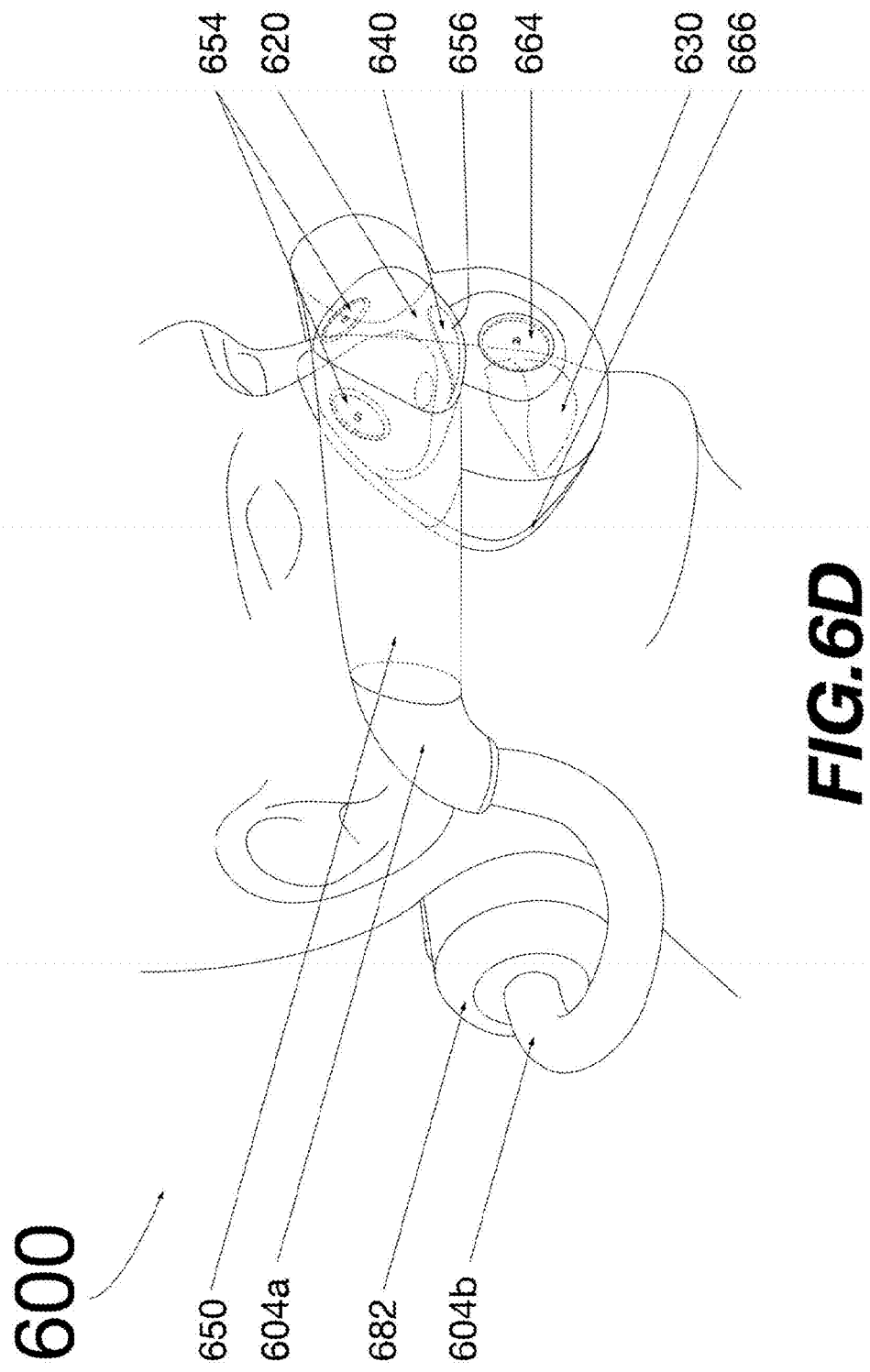
FIG. 6D is an illustration of the respirator 600 where the outer wall is made transparent.

As shown in FIG. 6D, the respirator 600 comprises a nasal aperture 620, a mouth aperture 630, a septum 640, a nasal fluid channel 650, two nasal inhalation valves 654, a nasal exhalation valve 656, an oral exhalation valves 664, an obturator 666, a first coupling member 604a, a second coupling member 604b, and an inhalation filter 682.

The first coupling member 604a connects the nasal fluid channel 650 with the second coupling member 604b. The second coupling member 604b is connected to the inhalation filter 682. In some embodiments, the first coupling member 604a is a joint or a connector. In some embodiments, the second coupling member 604b is a pipe.

Figure 6E:
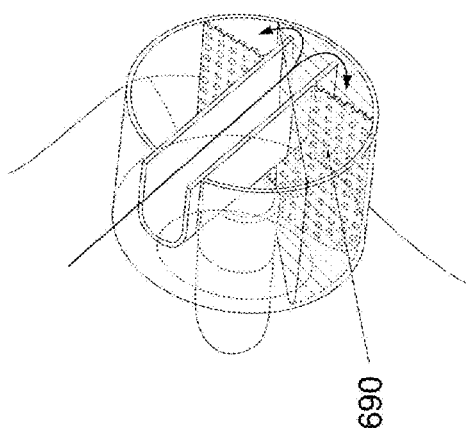
FIG. 6E is an illustration of a filter with liquid medium 690.
Figure 6F:
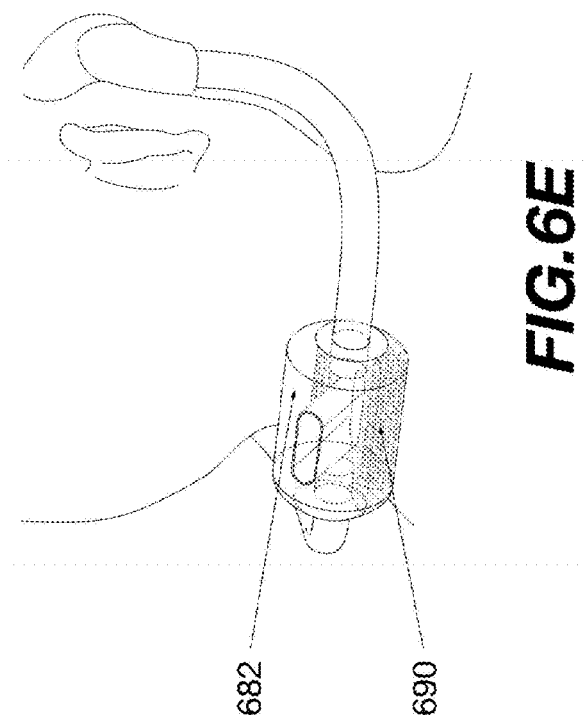
FIG. 6F is a cross-sectional view of the filter shown in FIG. 6A. The arrow shows the filtration pathway for inhalation.

FIGS. 6E-6F show the inhalation filter 682. Notably, the inlet for inhaled air is disposed at a predetermined angle relative to the ground. The liquid medium 690 is disposed on the bottom of the inhalation filter 682. As the inhaled air flows through the liquid medium 690, the inhaled air gets filtered.

When inhaling through the nose, under the action of negative relative pressure, the nasal inhalation valves 654 open, and air enters the inhalation filter 682, gets filtered, then enters the second coupling member 604b, the first coupling member 604a, the nasal fluid channel 650, and the nasal aperture 620. When inhaling through the mouth, in addition to the above process, the nasal exhalation valve 656 opens, and filtered air entered the mouth aperture 630.

When exhaling through the nose, under the influence of positive relative pressure, the nasal inhalation valves 654 close, and the nasal exhalation valve 656 and the oral exhalation valve 664 open. The exhaled air enters the mouth aperture 630 and exits through the oral exhalation valve 664. When exhaling through the mouth, under the influence of positive relative pressure, the nasal exhalation valve 656 closes and the oral exhalation valve 664 opens, thereby permitting the exhaled air to exit through the oral exhalation valve 664.

After each use or a plurality of uses, the respirator 600 can be disassembled, washed, and filled with a clean liquid medium for future use.

In some embodiments, instead of a liquid medium, a granular substance or a granular mixture, for example activated carbon, can be used as a filter material.

Figure 6G:
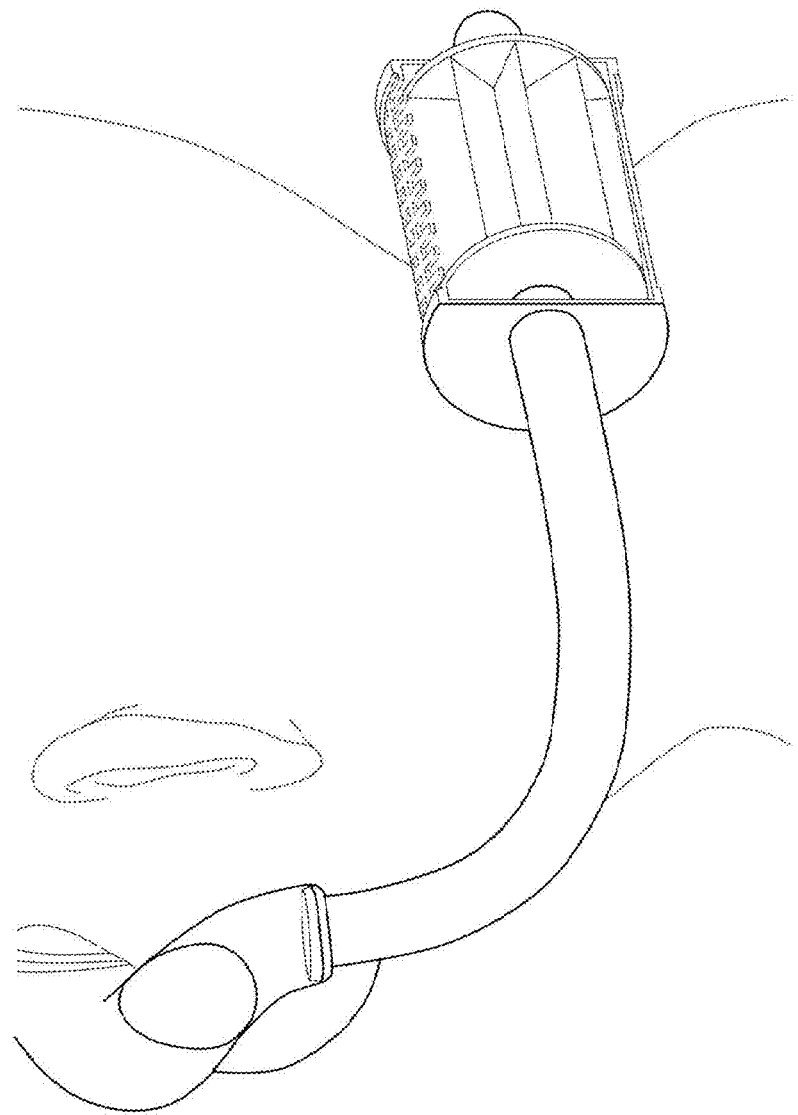
FIG. 6G is an illustration showing an inhalation filter with a filter cartridge.

In some embodiments, for example, at sub-zero ambient temperatures, standard filter cartridges can be used in the half mask of the same design. FIG. 6G shows an example of an industrial respirator with a filter cartridge, which is a standard filter made of corrugated material.

In order to reduce the cost of operation and user convenience, filter elements for a respirator can be assembled from rolled filter materials to form a roll filter. In some embodiments, the filter can be a roll filter, where a filter element is rolled into a three-dimensional structure. For example, the filter elements can be located horizontally, and not vertically, as shown in FIGS. 7A-7C. In FIG. 7A, one inhalation filter is disposed on each side of the nose. As shown in FIGS. 7B-7C, in contrast to standard filter use, the air does not move across the filtering material, but moves along the filtering material. In this way, the filtration properties (e.g., thinness of filtration and dust capacity) are improved.

Figure 8B:
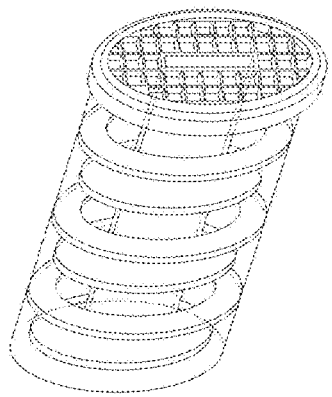
FIG. 8B is an illustration of a droplet separator suitable for removing large aerosol particles that have high adhesion (e.g., a saliva particle or a sputum particle).
Figure 8C:
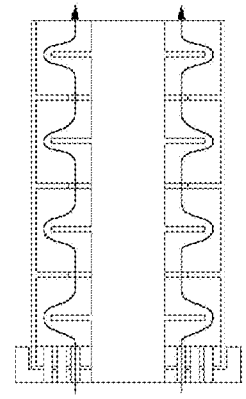
FIG. 8C is an illustration of the air flow in the droplet separator of FIG. 8B. The arrows indicate the air flow direction.
Figure 8A:
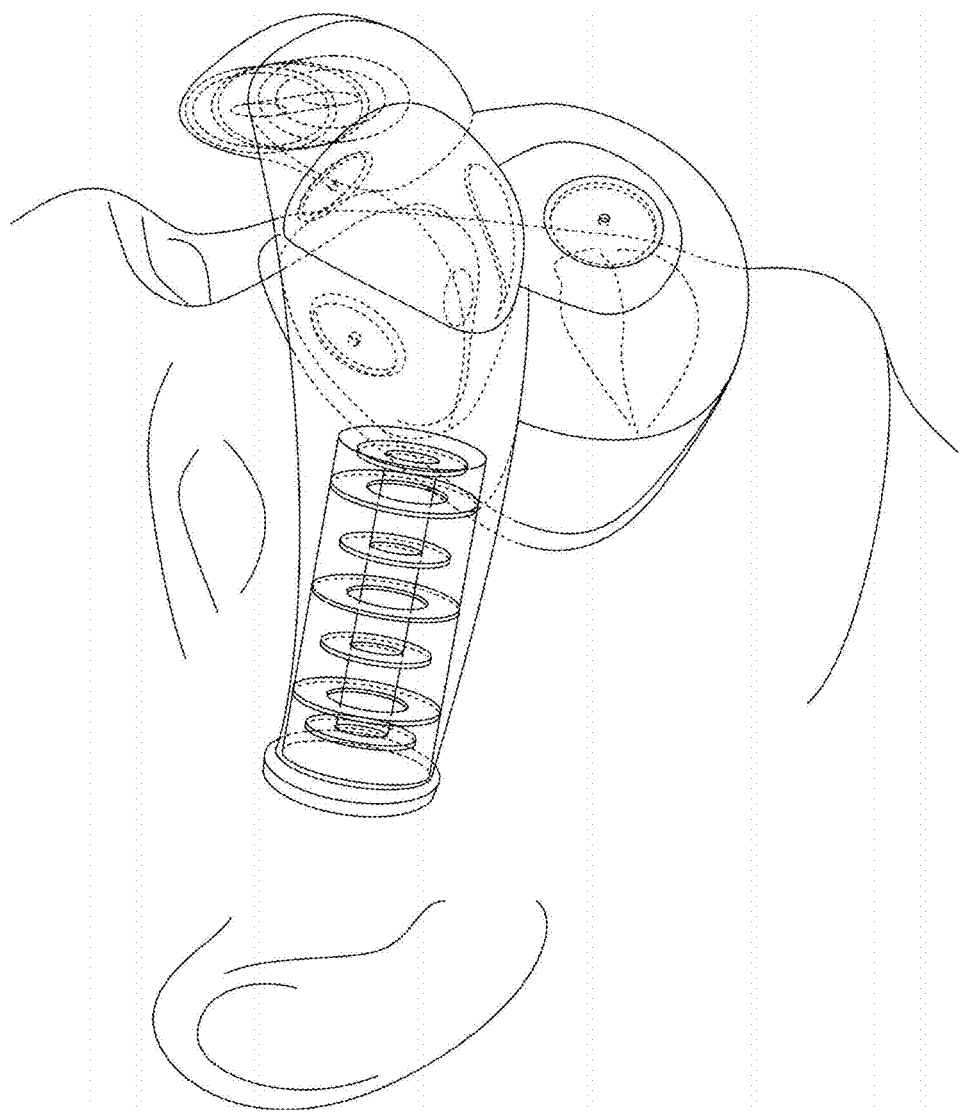
FIG. 8A is an illustration of a respirator having droplet separators as inhalation filters.

In some embodiments, when it is necessary to filter large aerosol particles that have high adhesion (e.g., particles of saliva, sputum), droplet separators can be used to clean the air by separation, as shown in FIGS. 8A-8C. As shown in FIG. 8C, the droplet separator comprises blocking structures on the air-flow pathway which permit the removal of large aerosol particles.

In some embodiments, the filter is configured to include a mesh. The mesh includes a plurality of cells. As the inhaled or exhaled air flows though the cells, particles are removed from the inhaled or exhaled air. The size of the cells determines the size of particles that the filter can remove from the air.

In some embodiments, the filter (e.g., an inhalation filter or an exhalation filter) can be a corrugated filter. The area of filter material is variable, e.g., from about one $cm^2$ to about 10,000 $cm^2$. The filter material can be of any type, depending of the filtration goal. For example, in order to filter aerosol particles, micro-fiberglass material or meltblown material can be used. To filter hazardous gases, activated charcoal can be used. To filter humid exhaled air we a Teflon-based membrane can be used, which can maintain its filtration properties when it is moisturized or wet.

Figure 11:
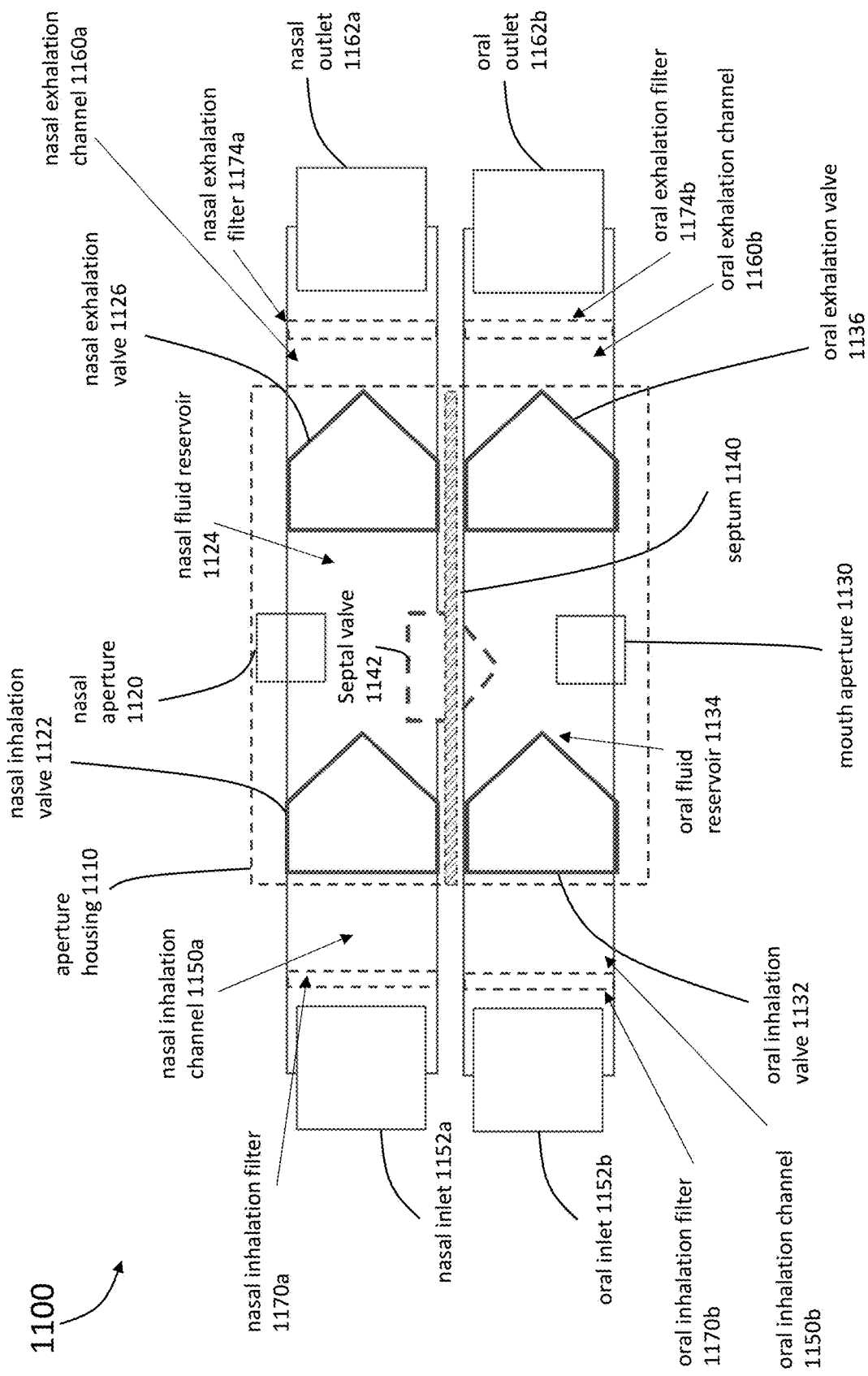
FIG. 11 is a schematic diagram illustrating a respirator 1100, in accordance with an embodiment.

FIG. 11 shows an embodiment of a respirator 1100 where inhalation can be done through the nose or mouth, each through a separate valve, and exhalation can also be done through the nose or mouth, each through a separate valve.

The respirator 1100 comprises: (a) a nasal aperture 1120, (b) a nasal inhalation valve 1122, (c) a nasal fluid reservoir 1124, (d) a nasal exhalation valve 1126, (e) a mouth aperture 1130, (f) an oral inhalation valve 1132, (g) an oral fluid reservoir 1134, (h) an oral exhalation valve 1136, (i) a nasal inhalation channel 1150a and an oral inhalation channel 1150b, (j) a nasal inhalation inlet 1152a and an oral inhalation inlet 1152b, (k) a nasal exhalation channel 1160a and an oral exhalation channel 1160b, and (l) a nasal exhalation outlet 1162a and an oral exhalation outlet 1162b.

The nasal aperture 1120 is configured to be disposed about a pair of nostrils of a user. The mouth aperture 1130 is configured to be disposed about a mouth of the user when the nasal aperture 1120 is disposed about the nostrils of the user. The respirator 1100 can further comprise an obturator (not shown) disposed on the circumferences of the nasal aperture 1120 and the mouth aperture 1130. The obturator is configured to form a seal around the nostrils and the mouth so that fluidic communication between (a) the nasal fluid reservoir 1124 and (b) the oral inhalation channel 1150a and the oral exhalation channel 1160a is prevented unless the nasal inhalation valve 1122 or the nasal exhalation valve 1126 is in an open configuration. Similarly, the obturator is configured to form a seal around the nostrils and the mouth so that fluidic communication between (a) the oral fluid reservoir 1134 and (b) the oral inhalation channel 1150b and the oral exhalation channel 1160b is prevented unless the oral inhalation valve 1132 or the oral exhalation valve 1136 is in an open configuration.

The respirator 1100 can optionally comprise a septum 1140 disposed between the nasal fluid reservoir 1124 and the oral fluid reservoir 1134. The septum 1140 is configured to prevent fluidic communication between the nasal fluid reservoir 1124 and the oral fluid reservoir 1134. The nasal fluid reservoir 1124 is configured to be in fluidic communication with the pair of nostrils. The oral fluid reservoir 1134 is configured to be in fluidic communication with the mouth of the user. In some embodiments, the septum 1140 can include an obturator configured to form a seal on the face of the user to prevent fluidic communication between the nasal fluid reservoir 1124 and the oral fluid reservoir 1134.

The nasal inhalation valve 1122 is disposed between the nasal fluid reservoir 1124 and the nasal inhalation channel 1150a that is in fluidic communication with the nasal inhalation inlet 1152a. The nasal inhalation valve 1122 is configured to transition between an open configuration and a closed configuration. In the open configuration, the nasal fluid reservoir 1124 is in fluidic communication with the nasal inhalation channel 1150a, and by extension, the nasal inhalation inlet 1152a. In the closed configuration, fluidic communication between the nasal fluid reservoir 1124 and the nasal inhalation channel 1150a, and by extension, the nasal inhalation inlet 1152a, is prevented. The nasal inhalation valve 1122 is configured to assume its open configuration in response to nasal inhalation by the user, and its closed configuration in response to nasal exhalation by the user, as described in more detail below.

The nasal exhalation valve 1126 is disposed between the nasal fluid reservoir 1124 and the nasal exhalation channel 1160a that is in fluidic communication with the nasal exhalation outlet 1162a. The nasal exhalation valve 1126 is configured to transition between an open configuration and a closed configuration. In the open configuration, the nasal fluid reservoir 1124 is in fluidic communication with the nasal exhalation channel 1160a, and by extension the nasal exhalation outlet 1162a. In the closed configuration, fluidic communication between the nasal fluid reservoir 1124 and the nasal exhalation channel 1160a, and by extension, the nasal exhalation outlet 1162a, is prevented. The nasal exhalation valve 1126 is configured to assume its open configuration in response to nasal exhalation by the user, and its closed configuration in response to nasal inhalation by the user.

The oral inhalation valve 1132 is disposed between the oral fluid reservoir 1134 and the oral inhalation channel 1150b that is in fluidic communication with the oral inhalation inlet 1152b. The oral inhalation valve 1132 is configured to transition between an open configuration and a closed configuration. In the open configuration, the oral fluid reservoir 1134 is in fluidic communication with the oral inhalation channel 1150b, and by extension, the oral inhalation inlet 1152b. In the closed configuration, fluidic communication between the oral fluid reservoir 1134 and the oral inhalation channel 1150b, and by extension, the oral inhalation inlet 1152b, is prevented. The oral inhalation valve 1132 is configured to assume its open configuration in response to oral inhalation by the user, and its closed configuration in response to oral exhalation by the user.

The oral exhalation valve 1136 is disposed between the oral fluid reservoir 1134 and the oral exhalation channel 1160b that is in fluidic communication with the oral exhalation outlet 1162b. The oral exhalation valve 1136 is configured to transition between an open configuration and a closed configuration. In the open configuration, the oral fluid reservoir 1134 is in fluidic communication with the oral exhalation channel 1160b, and by extension, the oral exhalation outlet 1162b. In the closed configuration, fluidic communication between the oral fluid reservoir 1134 and the oral exhalation channel 1160b, and by extension, the oral exhalation outlet 1162, is prevented. The oral exhalation valve 1136 is configured to assume its open configuration in response to oral exhalation by the user, and its closed configuration in response to oral inhalation by the user.

In some implementations, the respirator 1100 further comprises an nasal inhalation filter 1170a disposed between (1) the nasal inhalation inlet 1152a and (2) the nasal inhalation valve 1122, and/or an oral inhalation filter 1170b disposed between (1) the oral inhalation inlet 1152b and (2) the oral inhalation valve 1132. In some implementations, the nasal inhalation filter 1170a is disposed within the nasal inhalation channel 1150a. In some implementations, the nasal inhalation filter 1170a is disposed at a distal end of the nasal inhalation channel 1150a. In some implementations, the oral inhalation filter 1170b is disposed within the oral inhalation channel 1150b. In some implementations, the oral inhalation filter 1170b is disposed at a distal end of the oral inhalation channel 1150b. The inhalation filter(s) 1170a/b are configured to filter the air entering the inhalation inlet(s) 1152a/b (e.g., to remove pathogens, particulates, or otherwise anything undesirable to the user).

The respirator 1100 can optionally comprise a nasal exhalation filter 1174a disposed between (1) the nasal exhalation outlet 1162a and (2) the nasal exhalation valve 1126, and/or an oral exhalation filter 1174b disposed between (1) the oral exhalation outlet 1162b and (2) the oral exhalation valve 1136. In some implementations, the nasal exhalation filter 1174a is disposed within the nasal exhalation channel 1160a. In some implementations, the nasal exhalation filter 1174a is disposed at a distal end of the nasal exhalation channel 1160a. In some implementations, the oral exhalation filter 1174b is disposed within the oral exhalation channel 1160b. In some implementations, the oral exhalation filter 1174b is disposed at a distal end of the oral exhalation channel 1160b. The exhalation filter(s) 1174a/b are configured to filter the air exiting the nasal exhalation valve 1126 and/or the oral exhalation valve 1136 (e.g., to remove pathogens, particulates, or otherwise anything undesirable to the environment around the user).

The inhalation filter(s) 1170a/b and exhalation filter(s) 1174a/b can operate accordingly a variety of filtering mechanisms. In some implementations, the inhalation filter(s) 1170a/b or the exhalation filter(s) 1174a/b are configured to include a liquid medium. In some implementations, the liquid medium is water or an antiseptic solution. Filtration can be achieved through a multi-stage process using various fluid properties. For example, large particles (e.g., dust, mucus, or saliva) can be removed by creating a vortex air that flows in the volume of the liquid, while finer filtering can be achieved through bubbling process when the air stream passes through a layer of unstable foam. In some implementations, the liquid medium can be replaced with a granular substance or a granular mixture, for example, activated carbon. In some implementations, the inhalation filter(s) 1170a/b or the exhalation filter(s) 1174a/b are configured to include a roll filter. In some implementations, the inhalation filter(s) 1170a/b or the exhalation filter(s) 1174a/b are configured to include a mesh. The inhalation filter(s) 1170a/b or the exhalation filter(s) 1174a/b can be positioned horizontally or vertically, or somewhere therebetween.

In some implementations, the nasal aperture 1120 and the mouth aperture 1130 are defined by an aperture housing 1110; the nasal inhalation channel 1150a and the oral inhalation channel 1150b, and the nasal fluid reservoir 1124 and the oral fluid reservoir 1134, can be connected to each other by the aperture housing 1110. Further, in some such implementations, the nasal inhalation valve 1122, the nasal exhalation valve 1126, the oral inhalation valve 1132, and/or the oral exhalation valve 1136, are disposed within the aperture housing 1110, as shown optionally in broken lines in FIG. 11.

In some implementations, the respirator 1100 further comprises a septal valve 1142 disposed within the septum 1140 (and defined by or disposed within the aperture housing 1110, when present) and configured to transition between an open configuration and a closed configuration. In the open configuration, the nasal fluid reservoir 1124 is in fluidic communication with the oral fluid reservoir 1134. In the closed configuration, fluidic communication between the nasal fluid reservoir 1124 and the oral fluid reservoir 1134 is prevented. The septal valve 1142 is configured to assume its open configuration in response to oral inhalation or nasal exhalation by the user, and its closed configuration in response to oral exhalation or nasal inhalation by the user. In some implementations, the septum 1140 extends from one end of the aperture housing 1110 (when present) to another (e.g., opposite) end of the aperture housing 1110 to fluidically isolate the nasal fluid reservoir from the oral fluid reservoir, with fluid communication therebetween available through the septal valve 1142, as described above.

While FIG. 11 only shows one septum, some implementations of the respirator 1100 can have two, three, four, or more septa. While FIG. 11 only shows one optional septal valve, some implementations of the respirator 1100 can have two, three, four, or more septal valves. While FIG. 11 only shows one nasal inhalation valve, some implementations of the respirator 1100 can have two, three, four, or more nasal inhalation valves. While FIG. 11 only shows one nasal exhalation valve, some implementations of the respirator 1100 can have two, three, four, or more nasal exhalation valves. While FIG. 11 only shows one oral inhalation valve, some implementations of the respirator 1100 can have two, three, four, or more oral inhalation valves. While FIG. 11 only shows one oral exhalation valve, some implementations of the respirator 1100 can have two, three, four, or more oral exhalation valves.

Generally, the operating principle of the respirator 1100 can be described as follows. When inhaling through the nose or mouth, under the influence of negative relative pressure, the nasal inhalation valve 1122 or the oral inhalation valve 1132 opens, and air enters from the nasal inhalation channel 1150a or the oral inhalation channel 1150b into the nasal fluid reservoir 1124 or the oral fluid reservoir 1134, respectively. The air previously passes through optional inhalation filter(s) 1170a/b from the space external to the respirator 1100. When the user exhales through the nose or mouth, under the influence of positive relative pressure, the nasal inhalation valve 1122 or the oral inhalation valve 1132 is closed, and the nasal exhalation valve 1126 or the oral exhalation valve 1136 opens, and air enters the nasal exhalation channel 1160a or the oral exhalation channel 1160b, respectively. The exhaled air exits the respirator 1100 through the outlets 1162a/b and optionally after passing through an exhalation filter(s) 1174a/b.

The outer layer of the housing is transparent, opaque, or a combination thereof (e.g., a portion of the outer layer facing the user's mouth may be transparent to aid in communication between the user and others, while other portions of the outer layer may be less transparent or opaque). The outer layer of the housing can be made of any suitable material, e.g., plastic, silicone, or the like.

The housing can be made, partially or whole, from breathable (filtering) material. In some implementations, the respirator 1100 is for single use. For example, the whole housing can be made of a spunbond meltblown spunbond (SMS) material.

In some implementations, the respirator 1100 is reusable. For example, a portion of the housing (e.g., the obturator) can be made of silicone and/or thermoplastic elastomer; another portion of the housing can be made of ABS plastic, or polyethylene terephthalate (PET) plastic; and valves can be made of silicone or rubber.

In some implementations, only the obturator and the coupling member (e.g., a strap) are configured to be in contact with the skin when the user wears the respirator 1100. In some implementations where additional components are in contact with the skin, these additional components can be made of an air permeable material.

Regardless of whether the respirator 1100 is for single use or reusable, in some implementations separate components are manufactured separately and then assembled into the respirator 1100.

Figure 12B:
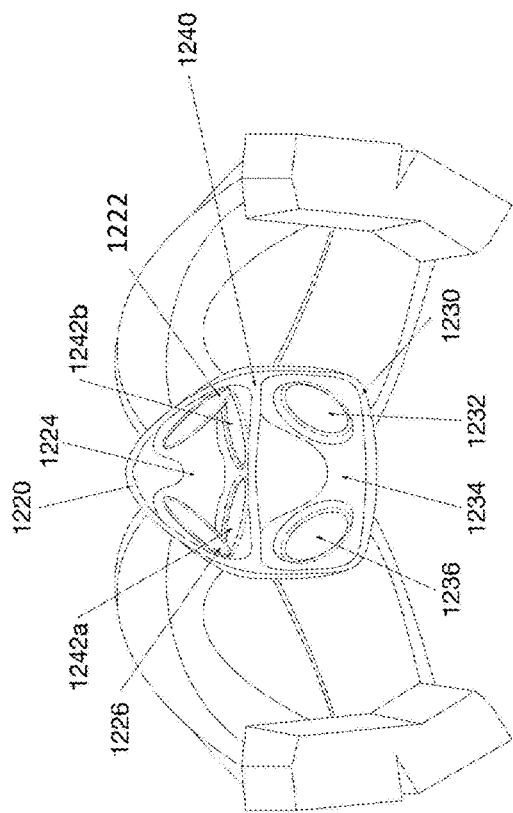
FIG. 12B is a rear view of the respirator 1200.
Figure 12A:
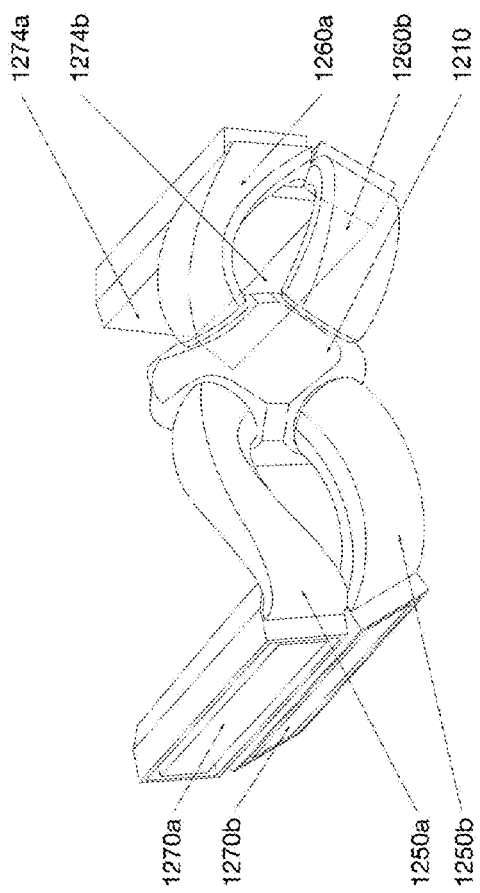
FIG. 12A is a front view of a respirator 1200, in accordance with an embodiment of FIG. 11

FIGS. 12A-12B show front and rear views of a respirator 1200 that comprises the features of the respirator 1100 shown in FIG. 11, according to an embodiment. As shown in FIGS. 12A-12B, the respirator 1200 comprises an aperture housing 1210, a nasal aperture 1220, a mouth aperture 1230, a septum 1240, a nasal inhalation channel 1250a, an oral inhalation channel 1250b, a nasal fluid reservoir 1224, an oral fluid reservoir 1234, a nasal exhalation channel 1260a, an oral exhalation channel 1260b, a nasal inhalation valve 1222, a nasal exhalation valve 1226, an oral inhalation valve 1232, an oral exhalation valve 1236, a nasal inhalation filter 1270a, a nasal exhalation filter 1274a, an oral inhalation filter 1270b, an oral exhalation filter 1274b, and two septal valves 1242a/b. Note that the nasal inhalation filter 1270a, the nasal exhalation filter 1274a, the oral inhalation filter 1270b, and the oral exhalation filter 1274b are installed in filter blocks.

The aperture housing 1210 defines the nasal aperture 1220 and the mouth aperture 1230. Each of the nasal inhalation channel 1250a, oral inhalation channel 1250b, nasal exhalation channel 1260a, and the oral exhalation channel 1260b, has its own housing defining a volume. Those four channels are interconnected by the aperture housing 1210.

The nasal inhalation valve 1222 and the nasal exhalation valve 1226 are configured to be disposed about the nose such that there is one nasal valve on each side of the nose. The septal valves 1242a/b are configured to be disposed below the nostrils such that there is one septum valve below each nostril. The oral inhalation valve 1232 and the oral exhalation valve 1236 are disposed about the mouth such that there is one oral valve on each side of the mouth.

In addition to FIGS. 5G, 6E, and 6F, embodiments of hydro-respirators are shown in FIGS. 14A-14B and FIGS. 15A-15B. As used herein, the term "hydro-respirator" refers to a respirator that uses a liquid medium for filtering inhaled air, exhaled air, or a combination thereof.

Figure 14B:
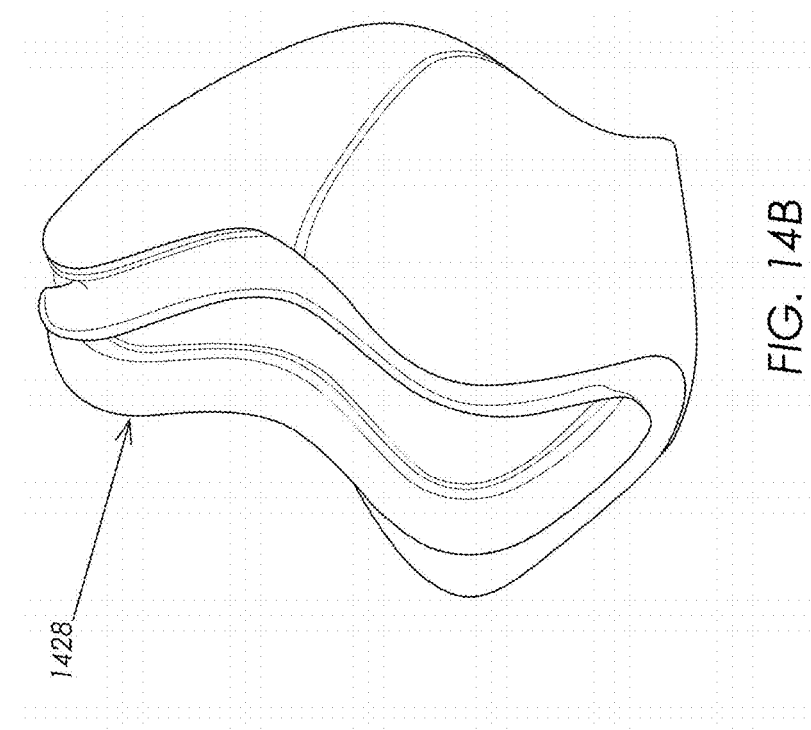
FIG. 14B shows an obturator 1428 of the hydro-respirator 1400.
Figure 14A:
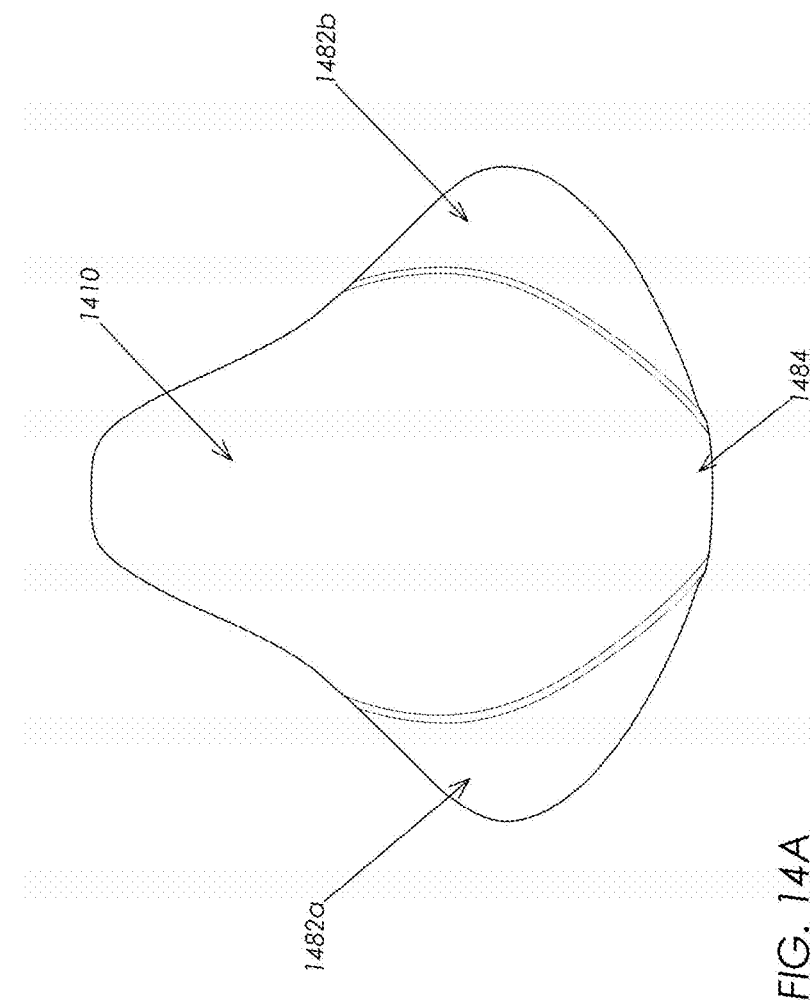
FIG. 14A is a front view of a hydro-respirator 1400.

In FIG. 14A, a hydro-respirator 1400 comprises an inhalation hydrofilter 1482a, an inhalation or exhalation hydrofilter 1482b, an aperture housing 1410, and an exhalation valve 1484. FIG. 14B shows an obturator 1428 that is configured to form a seal around the nostrils and mouth of a user. As used herein, the term "hydrofilter" refers to a filter that uses a liquid medium for filtration. In some embodiments, the liquid medium is water. In some embodiments, the liquid medium is an antiseptic solution.

Figure 15A:
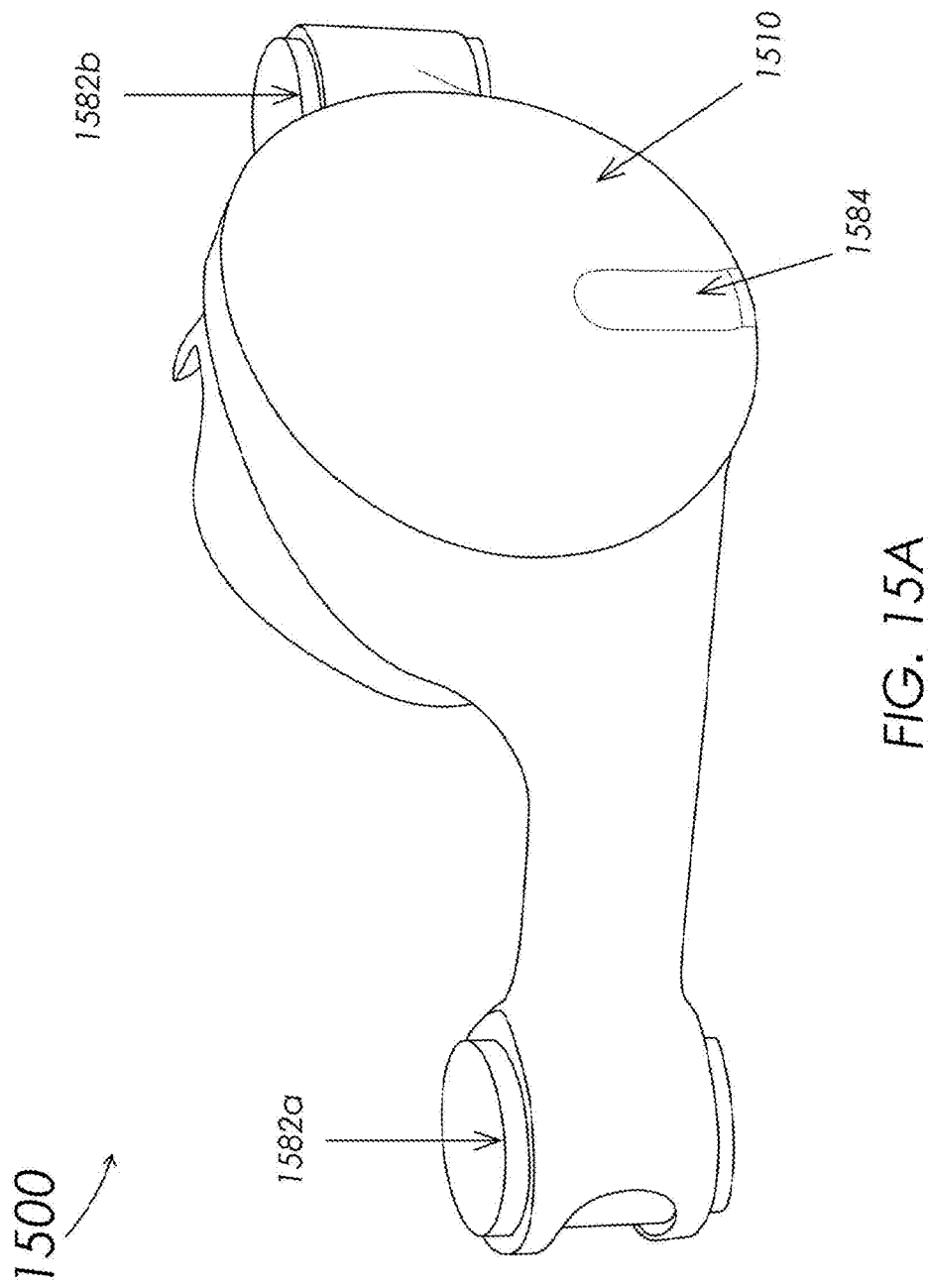
FIGS. 15A-15B show a perspective view (FIG. 15A) and a top-down view (FIG. 15B) of a hydro-respirator 1500.
Figure 15B:
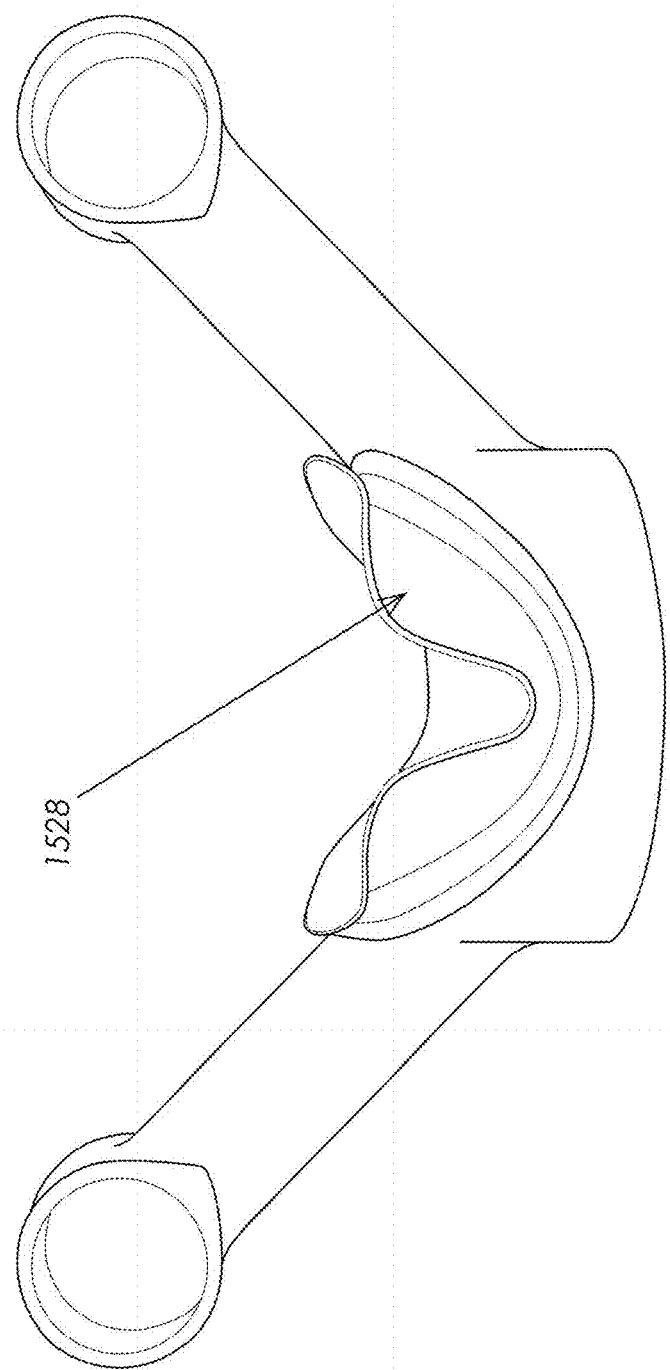

In FIG. 15A, a hydro-respirator 1500 comprises an inhalation hydrofilter 1582a, an inhalation or exhalation hydrofilter 1582b, an aperture housing 1510, and an exhalation valve 1584. FIG. 15B shows an obturator 1528 that is configured to form a seal around the nostrils and mouth of a user.

Different filters are described in conjunction with the drawings. It should not be construed that those filters can only be used in those respirators depicted in the drawings. Rather the filters can be used in any one of the respirators described throughout the present application.

Various configurations of filters, filter housings, inlets and outlets, are described in conjunction with the drawings. It should be understood that in any of the embodiments described herein, the filters can be exposed to the environment, and those filters can define the inlet and outlets, rather than the inlets and outlets being defined by a separate housing or filter housing.

Similarly, different head mounts are described in conjunction with the drawings. It should not be construed that those head mounts can only be used in those respirators depicted in the drawings. Rather the head mounts can be used in any one of the respirators described throughout the present application.

Figure 13B:
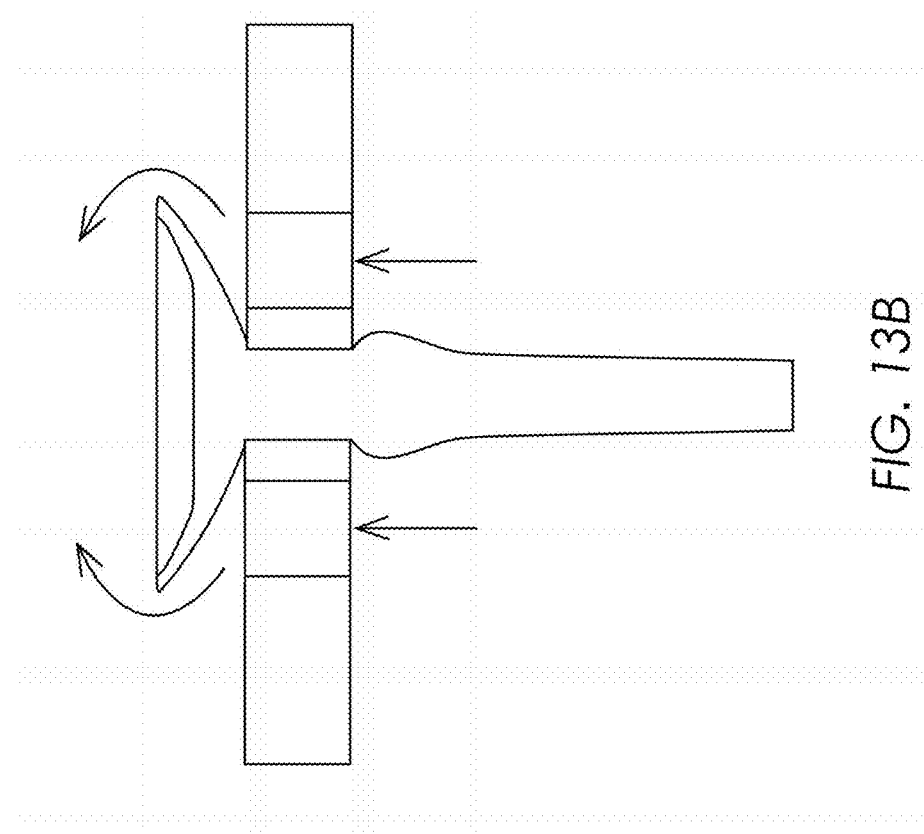
FIGS. 13A-13B are schematic diagrams showing an umbrella one-way valve, where the valve is closed (FIG. 13A) and open (FIG. 13B).
Figure 13A:
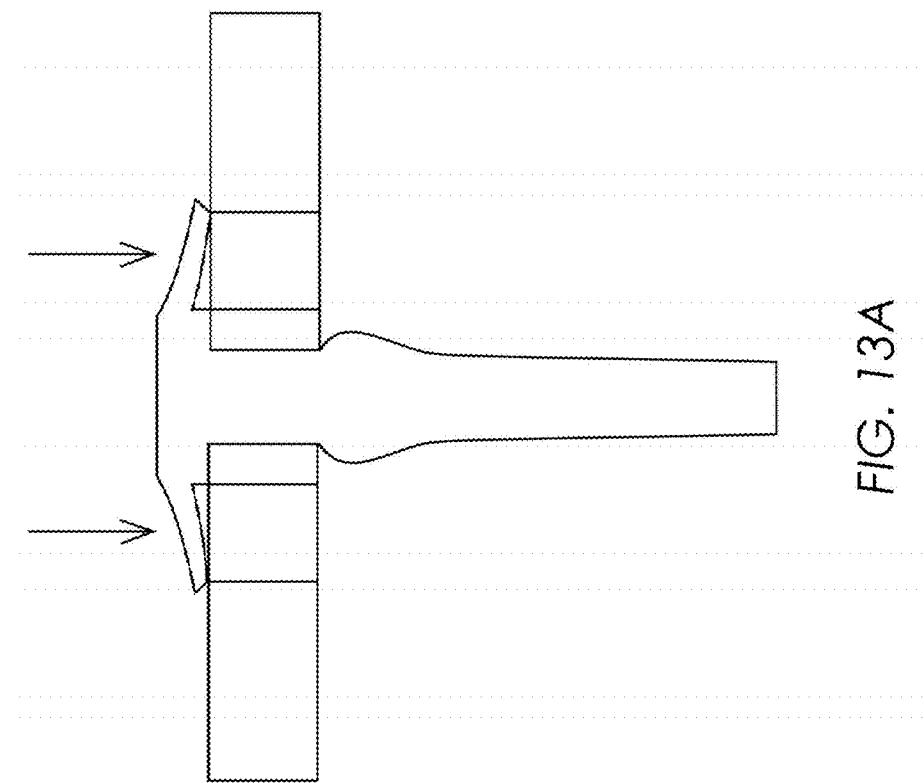

In some implementations, the valve (e.g., an inhalation valve, an exhalation valve, or a septal valve) described throughout the present application is a one-way valve. The one-way valve thus permits the transition from an open configuration to a closed configuration, and vice versa. The one-way valve can utilize any known designs, including but not limited to, umbrella, duckbill, mushroom, flap, Archimedes' screw, and membrane. In some implementations, the one-way valve is an umbrella valve, e.g., having an opening pressure of about two to about five pascals. FIGS. 13A-13B show an umbrella one-way valve, where the valve is closed (FIG. 13A) and open (FIG. 13B).

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto; inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or"

as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The terms "substantially," "approximately," and "about" used throughout this Specification and the claims generally mean plus or minus 10% of the value stated, e.g., about 100 would include 90 to 110.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. An apparatus, comprising:
a mouth aperture configured to be disposed in fluid communication with a mouth of a user;
a nasal aperture configured to be disposed in fluid communication with one or both nostrils of the user when the mouth aperture is disposed in fluid communication with the mouth of the user;
a nasal fluid reservoir configured to be in fluidic communication with the one or both nostrils;
an oral fluid reservoir configured to be in fluidic communication with the mouth of the user;
a septum disposed between the nasal fluid reservoir and the oral fluid reservoir;
a septal inhalation valve disposed within the septum and configured to transition between a septal inhalation valve open configuration in which the nasal fluid reservoir is in fluidic communication with the oral fluid reservoir, and a septal inhalation valve closed configuration in which fluidic communication between the nasal fluid reservoir and the oral fluid reservoir is substantially prevented, the septal inhalation valve being configured to assume the septal inhalation valve open configuration in response to oral inhalation or nasal exhalation by the user, and the septal inhalation valve closed configuration in response to oral exhalation or nasal inhalation by the user;
a first nasal inhalation valve disposed between the nasal fluid reservoir and a first inhalation channel that is in fluidic communication with a first inhalation inlet, and configured to transition between a first nasal inhalation valve open configuration in which the nasal fluid reservoir is in fluidic communication with the first inhalation channel, and a first nasal inhalation valve closed configuration in which fluidic communication between the nasal fluid reservoir and the first inhalation channel is substantially prevented, the first inhalation inlet being configured to be disposed above the user's shoulders when the mouth aperture is disposed in fluid communication with the mouth of the user and the nasal aperture is disposed in fluid communication with the one or both nostrils;
a second nasal inhalation valve disposed between the nasal fluid reservoir and a second inhalation channel that is in fluidic communication with a second inhalation inlet, and configured to transition between a second nasal inhalation valve open configuration in which the nasal fluid reservoir is in fluidic communication with the second inhalation channel, and a second nasal inhalation valve closed configuration in which fluidic communication between the nasal fluid reservoir and the second inhalation channel is substantially prevented, the second inhalation inlet being configured to be disposed above the user's shoulders when the mouth aperture is disposed in fluid communication with the mouth of the user and the nasal aperture is disposed in fluid communication with the one or both nostrils;
a first oral exhalation valve disposed between the oral fluid reservoir and a first exhalation channel that is in fluidic communication with a first exhalation outlet, and configured to transition between a first oral exhalation valve open configuration in which the oral fluid reservoir is in fluidic communication with the first exhalation channel, and a first oral exhalation valve closed configuration in which fluidic communication between the oral fluid reservoir and the first exhalation channel is substantially prevented, the first exhalation outlet being configured to be disposed above the user's shoulders when the mouth aperture is disposed in fluid communication with the mouth of the user and the nasal aperture is disposed in fluid communication with the one or both nostrils;
a second oral exhalation valve disposed between the oral fluid reservoir and a second exhalation channel that is in fluidic communication with a second exhalation outlet, and configured to transition between a second oral exhalation valve open configuration in which the oral fluid reservoir is in fluidic communication with the second exhalation channel, and a second oral exhalation valve closed configuration in which fluidic communication between the oral fluid reservoir and the second exhalation channel is substantially prevented, the second exhalation outlet being configured to be disposed above the user's shoulders when the mouth aperture is disposed in fluid communication with the mouth of the user and the nasal aperture is disposed in fluid communication with the one or both nostrils;
a first inhalation filter disposed upstream the first nasal inhalation valve to filter ambient air drawn into the first inhalation inlet from an ambient environment;
a second inhalation filter disposed upstream the second nasal inhalation valve to filter ambient air drawn into the second inhalation inlet from the ambient environment;
a first exhalation filter disposed downstream the first oral exhalation valve to filter air exhaled by the user for discharge to the ambient environment;
a second exhalation filter disposed downstream the second oral exhalation valve to filter air exhaled by the user for discharge to the ambient environment;
a first filter block housing containing the first inhalation filter and the first exhalation filter; and
a second filter block housing containing the second inhalation filter and the second exhalation filter,
the first inhalation channel, the second inhalation channel, the first exhalation channel, and the second exhalation channel each being defined within respective housings distinct from one another;
the first and second nasal inhalation valves being configured to assume the first and second nasal inhalation valve open configurations, respectively, in response to nasal inhalation by the user, and the first and second nasal inhalation valve closed configurations, respectively, in response to nasal exhalation by the user,
the first and second oral exhalation valves being configured to assume the first and second oral exhalation valve open configurations, respectively, in response to oral exhalation by the user, and the first and second oral exhalation valve closed configurations, respectively, in response to oral inhalation by the user.

2. The apparatus of claim 1, further comprising a housing defining an inner layer and an outer layer, and a volume defined therebetween, the inner layer defining the nasal aperture and mouth aperture.

3. The apparatus of claim 1, wherein at least one of the first inhalation filter or the second inhalation filter includes a first container configured to contain a liquid medium.

4. The apparatus of claim 1, wherein:
the first inhalation filter and the first exhalation filter are configured to be disposed adjacent a first cheek of the user's face, and the second inhalation filter and the second exhalation filter configured to be disposed adjacent a second cheek of the user's face.

5. The apparatus of claim 1, wherein the first and second inhalation inlets and the first and second exhalation outlets are configured to be disposed in a posterior region of the user's head when the mouth aperture is disposed in fluid communication with the mouth of the user and the nasal aperture is disposed in fluid communication with the one or both nostrils.

6. The apparatus of claim 1, wherein the first inhalation channel and the first exhalation channel are configured to extend about and terminate adjacent to a first side of the user's head, and the second inhalation channel and the second exhalation channel are configured to extend about and terminate adjacent to a second side, opposite the first side, of the user's head.

7. The apparatus of claim 1, further comprising a head mount configured to be disposed about a parietal part of a user's head.

8. The apparatus of claim 1, wherein the first inhalation inlet is configured to be disposed immediately adjacent the user's head when the mouth aperture is disposed in fluid communication with the mouth of the user and the nasal aperture is disposed in fluid communication with the one or both nostrils such that the air immediately surrounding the user enters the first inhalation inlet during inhalation.

9. The apparatus of claim 1, wherein the first exhalation outlet is configured to be disposed immediately adjacent the user's head when the mouth aperture is disposed in fluid communication with the mouth of the user and the nasal aperture is disposed in fluid communication with the one or both nostrils such that fluid exhaled by the user exits the first exhalation outlet immediately surrounding the user.

10. The apparatus of claim 1, wherein first inhalation channel housing and the first exhalation channel housing are distinct such that a first space void of material exists therebetween, and the second inhalation channel housing and the second exhalation channel housing are distinct such that a second space void of material exists therebetween.

11. The apparatus of claim 1, wherein the septal inhalation valve is an umbrella valve.

12. The apparatus of claim 1, further comprising:
a first inhalation filter disposed upstream the first nasal inhalation valve to filter ambient air drawn into the first inhalation channel from an ambient environment, the first inhalation filter configured to be disposed adjacent a first cheek of the user's face; and
a second inhalation filter disposed upstream the second nasal inhalation valve to filter ambient air drawn into the second inhalation channel, the second inhalation filter configured to be disposed adjacent a second cheek of the user's face.

13. The apparatus of claim 1, wherein the first inhalation channel housing and the second inhalation channel housing are formed of rigid plastic.

14. The apparatus of claim 13, wherein the rigid plastic includes at least one of acrylonitrile butadiene styrene (ABS) plastic or polyethylene terephthalate (PET) plastic.

15. A respirator, comprising:
a mouth aperture configured to be disposed in fluid communication with a mouth of a user;
a nasal aperture configured to be disposed in fluid communication with one or both nostrils of the user when the mouth aperture is disposed in fluid communication with the user;
a nasal fluid reservoir configured to be in fluidic communication with the one or both nostrils;
an oral fluid reservoir configured to be in fluidic communication with the mouth of the user;
a nasal inhalation valve disposed between the nasal fluid reservoir and an inhalation inlet, and configured to transition between a nasal inhalation valve open configuration in which the nasal fluid reservoir is in fluidic communication with the inhalation inlet, and a nasal inhalation valve closed configuration in which fluidic communication between the nasal fluid reservoir and the inhalation inlet is prevented, the inhalation inlet being configured to receive air from an environment immediately surrounding the user when the user inhales while wearing the respirator;
an oral exhalation valve in fluid communication with the oral fluid reservoir and configured to transition between an oral exhalation valve open configuration in which the oral fluid reservoir is in fluidic communication with the environment via the oral exhalation valve, and an oral exhalation valve closed configuration in which fluidic communication between the oral fluid reservoir and the environment via the oral exhalation valve is substantially prevented, the oral exhalation valve being configured to direct air to the environment immediately surrounding the user when the user exhales while wearing the respirator and the oral exhalation valve is in the oral exhalation valve open configuration;

a septum disposed between the nasal fluid reservoir and the oral fluid reservoir;

a septal inhalation valve disposed within the septum and configured to transition between a septal inhalation valve open configuration in which the nasal fluid reservoir is in fluidic communication with the oral fluid reservoir, and a septal inhalation valve closed configuration in which fluidic communication between the nasal fluid reservoir and the oral fluid reservoir is substantially prevented, the septal inhalation valve being configured to assume the septal inhalation valve open configuration in response to oral inhalation or nasal exhalation by the user, and septal inhalation valve closed configuration in response to oral exhalation or nasal inhalation by the user, the nasal inhalation valve being configured to assume the nasal inhalation valve open configuration in response to nasal inhalation by the user, and the nasal inhalation valve closed configuration in response to nasal exhalation by the user, the oral exhalation valve being configured to assume the oral exhalation valve open configuration in response to oral exhalation by the user, and the oral exhalation valve closed configuration in response to oral inhalation by the user;

an inhalation filter disposed upstream of the nasal inhalation valve to filter ambient air drawn into the nasal fluid reservoir;

an exhalation filter disposed downstream of the oral exhalation valve to filter air exhaled by the user; and a filter block housing containing both the inhalation filter and the exhalation filter.

16. The respirator of claim 15, wherein at least one of the inhalation filter or the exhalation filter is configured to include a liquid medium.

17. The respirator of claim 16, wherein the liquid medium is water or an antiseptic solution.

18. The respirator of claim 15, wherein the exhalation filter is configured to include a liquid medium.

19. The respirator of claim 18, wherein the liquid medium is water or an antiseptic solution.

20. The respirator of claim 15, wherein the inhalation inlet is configured to terminate posterior to an ear of the user when the mouth aperture is disposed in fluid communication with the mouth of the user.

21. The respirator of claim 15, further comprising an obturator disposed on the circumferences of the nasal aperture and the mouth aperture, the obturator being configured to form a seal around the nostrils and the mouth.

22. The respirator of claim 15, further comprising a housing defining an inner layer and an outer layer, and a volume defined therebetween, the inner layer defining the nasal aperture and mouth aperture.

23. The respirator of claim 15, wherein the housing defines the inhalation inlet and the exhalation outlet.

24. The respirator of claim 15, further comprising a head mount configured to be disposed about a parietal part of a user's head.

25. The respirator of claim 15, wherein the first inhalation inlet and the first exhalation outlet are configured to be disposed above the user's shoulders when the respirator is worn by the user.

26. The respirator of claim 15, wherein the inhalation filter and the exhalation filter are integral.

27. An apparatus, comprising:

a mouth aperture configured to be disposed in fluid communication with a mouth of a user;

a nasal aperture configured to be disposed in fluid communication with one or both nostrils of the user when the mouth aperture is disposed in fluid communication with the mouth of the user;

a nasal fluid reservoir configured to be in fluidic communication with the one or both nostrils;

an oral fluid reservoir configured to be in fluidic communication with the mouth of the user;

a septum disposed between the nasal fluid reservoir and the oral fluid reservoir;

a septal inhalation valve disposed within the septum and configured to transition between a septal inhalation valve open configuration in which the nasal fluid reservoir is in fluidic communication with the oral fluid reservoir, and a septal inhalation valve closed configuration in which fluidic communication between the nasal fluid reservoir and the oral fluid reservoir is substantially prevented, the septal inhalation valve being configured to assume the septal inhalation valve open configuration in response to oral inhalation or nasal exhalation by the user, and the septal inhalation valve closed configuration in response to oral exhalation or nasal inhalation by the user;

a first nasal inhalation valve disposed between the nasal fluid reservoir and a first inhalation channel that is in fluidic communication with a first inhalation inlet, and configured to transition between a first nasal inhalation valve open configuration in which the nasal fluid reservoir is in fluidic communication with the first inhalation channel, and a first nasal inhalation valve closed configuration in which fluidic communication between the nasal fluid reservoir and the first inhalation channel is substantially prevented, the first inhalation inlet being configured to be disposed above the user's shoulders when the mouth aperture is disposed in fluid communication with the mouth of the user and the nasal aperture is disposed in fluid communication with the one or both nostrils;

a second nasal inhalation valve disposed between the nasal fluid reservoir and a second inhalation channel that is in fluidic communication with a second inhalation inlet, and configured to transition between a second nasal inhalation valve open configuration in which the nasal fluid reservoir is in fluidic communication with the second inhalation channel, and a second nasal inhalation valve closed configuration in which fluidic communication between the nasal fluid reservoir and the second inhalation channel is substantially prevented, the second inhalation inlet being configured to be disposed above the user's shoulders when the mouth aperture is disposed in fluid communication with the mouth of the user and the nasal aperture is disposed in fluid communication with the one or both nostrils;

a first oral exhalation valve disposed between the oral fluid reservoir and a first exhalation channel that is in fluidic communication with an first exhalation outlet, and configured to transition between a first oral exhalation valve open configuration in which the oral fluid reservoir is in fluidic communication with the first exhalation channel, and a first oral exhalation valve closed configuration in which fluidic communication between the oral fluid reservoir and the first exhalation channel is substantially prevented, the first exhalation outlet being configured to be disposed above the user's shoulders when the mouth aperture is disposed in fluid communication with the mouth of the user and the nasal aperture is disposed in fluid communication with the one or both nostrils;

a second oral exhalation valve disposed between the oral fluid reservoir and a second exhalation channel that is in fluidic communication with a second exhalation outlet, and configured to transition between a second oral exhalation valve open configuration in which the oral fluid reservoir is in fluidic communication with the second exhalation channel, and a second oral exhalation valve closed configuration in which fluidic communication between the oral fluid reservoir and the second exhalation channel is substantially prevented, the second exhalation outlet being configured to be disposed above the user's shoulders when the mouth aperture is disposed in fluid communication with the mouth of the user and the nasal aperture is disposed in fluid communication with the one or both nostrils;

a first inhalation filter disposed upstream the first nasal inhalation valve to filter ambient air drawn into the first inhalation channel from an ambient environment;

a second inhalation filter disposed upstream the second nasal inhalation valve to filter ambient air drawn into the second inhalation channel;

a first exhalation filter disposed downstream the first oral exhalation valve to filter air exhaled by the user into the first exhalation channel for discharge to the ambient environment; and a second exhalation filter disposed downstream the second oral exhalation valve to filter air exhaled by the user into the second exhalation channel for discharge to the ambient environment, the first inhalation filter and the first exhalation filter sharing a first filter block housing, and the second inhalation filter and the second exhalation filter sharing a second filter block housing, the first and second nasal inhalation valves being configured to assume the first and second nasal inhalation valve open configurations, respectively, in response to nasal inhalation by the user, and the first and second nasal inhalation valve closed configurations, respectively, in response to nasal exhalation by the user, the first and second oral exhalation valves being configured to assume the first and second oral exhalation valve open configurations, respectfully, in response to oral exhalation by the user, and the first and second oral exhalation valve closed configurations, respectfully, in response to oral inhalation by the user.

28. The apparatus of claim 27, wherein the first inhalation filter and the first exhalation filter are configured to be disposed adjacent a first cheek of the user's face, and the second inhalation filter and the second exhalation filter configured to be disposed adjacent a second cheek of the user's face.

* * * * *